United States Patent [19]
Kosak

[11] Patent Number: 6,048,736
[45] Date of Patent: Apr. 11, 2000

[54] CYCLODEXTRIN POLYMERS FOR CARRYING AND RELEASING DRUGS

[76] Inventor: Kenneth M. Kosak, 3194 S. 4400 West, West Valley City, Utah 84120

[21] Appl. No.: 09/223,055

[22] Filed: Dec. 30, 1998

Related U.S. Application Data

[63] Continuation-in-part of application No. 09/067,921, Apr. 29, 1998, abandoned.
[51] Int. Cl.$^7$ .................... G01N 33/536; G01N 33/564; A01N 43/04; A61K 31/715
[52] U.S. Cl. .............................. 436/536; 436/507; 514/58
[58] Field of Search ..................................... 436/536, 507; 514/58

[56] References Cited

FOREIGN PATENT DOCUMENTS

91/05605   5/1991   WIPO .

*Primary Examiner*—Jeffrey Stucker
*Assistant Examiner*—Brett Nelson

[57] ABSTRACT

This invention discloses methods for preparing compositions of cyclodextrin polymers for carrying drugs and other active agents. Methods are also disclosed for preparing cyclodextrin polymer carriers that release drugs under controlled conditions. The invention also discloses methods for preparing compositions of cyclodextrin polymer carriers that are coupled to biorecognition molecules for targeting the delivery of drugs to their site of action.

The advantages of the water soluble (or colloidal) cyclodextrin polymer carrier are:

(1) Drugs can be used that are designed for efficacy without conjugation requirements.

(2) It will allow the use of drugs designed solely for efficacy without regard for solubility.

(3) Unmodified drugs can be delivered as macromolecules and released within the cell.

(4) Drugs can be targeted by coupling the carrier to biorecognition molecules.

(5) Synthesis methods are independent of the drug to facilitate multiple drug therapies.

9 Claims, No Drawings

CYCLODEXTRIN POLYMERS FOR CARRYING AND RELEASING DRUGS

RELATED PATENT APPLICATIONS

This is a continuation-in-part of patent application Ser. No. 09/067,921, filed Apr. 29, 1998 now abandoned. The contents of which are hereby incorporated herein by reference.

FIELD OF THE INVENTION

This invention discloses methods for preparing compositions of cyclodextrin polymers for carrying drugs and other agents. Methods are also disclosed for preparing cyclodextrin polymer carriers that release drugs under controlled conditions. The invention also discloses methods for preparing compositions of cyclodextrin polymer carriers that are coupled to biorecognition molecules for targeting the delivery of drugs to their site of action.

DESCRIPTION OF THE PRIOR ART

The pharmacokinetics of many anti-viral and anti-cancer drugs that penetrate cells through diffusion are not easily controlled. Therefore, there is a need for carriers of drugs and active agents that facilitate their solubility, delivery and effectiveness. When drugs are bound to polymers of the prior art they are taken up at the cell surface by endosomes (receptosomes) and transferred to the lysosomal compartment. This permits modulation of drug uptake through cell surface properties. Also, drug release can be controlled using specific enzymes and other conditions within the cell.

Drugs and other active agents delivered as macromolecules through polymer carriers have gained acceptance as a way for improving cancer chemotherapy and other drug therapies. Also, the prior art now employs drug-antibody or drug-polypeptide conjugates to re-direct anti-cancer and other agents to selected target cells.

Cyclodextrins and their derivatives have been shown to enhance the aqueous solubility of unmodified drugs and reduce the side effects in vivo. Cyclodextrin derivatives are well tolerated parenterally, especially hydroxypropyl cyclodextrin (HPCD), which is reported to have toxicity approaching that of glucose. The NIH currently holds a patent (U.S. Pat. No. 4,727,064, issued 1988) for the improvement of drug preparations using cyclodextrins. Cyclodextrins and their derivatives have been mixed with many drugs in an effort to utilize these properties. However, because individual cyclodextrins and even individual cyclodextrin derivatives easily dissociate from the drug with dilution, many of the advantages of cyclodextrins are limited with parenteral treatment.

The prior art of cyclodextrins has disclosed their use in labeling materials for in vitro testing (Kosak, PCT WO 91/05605, 1991), and in drug preparations (Hirai, et al, U.S. Pat. Nos. 4,523,031 and 4,523,037).

The preparation and use of individual cyclodextrins conjugated to biorecognition molecules as drug carriers is disclosed by Weinshenker, U.S. Pat. No. 5,068,227, 1991, where each coupling site is limited to one drug molecule. However, Weinshenker makes no disclosures or suggestions for any cyclodextrin polymers and they cannot be made with the synthesis methods disclosed. When drugs and other active agents as guest molecules are noncovalently bonded to the individual cyclodextrins of the prior art, they are subject to excessive dissociation, which results in uncontrolled release of drug even before the carriers reach their targets.

Review articles on the pharmaceutical applications of cyclodextrins have identified many problems due to the high turnover rate between inclusion complex formation and dissociation. Stella, V. J., et al., Pharmaceut. Res. 14, 556–567 (1997), report that even with the strongest theoretical binding constants, as soon as the complex of free cyclodextrin and drug is diluted in the bloodstream, over 30% is calculated to dissociate. Also, Rajewski, R., et al, J. Pharm. Sci. 85, 1142–1169 (1996), solubilized the anti-cancer drug Taxol with cyclodextrins. They reported on page 1145 that "any attempt to dilute the samples resulted in erratic precipitation" due to competitive displacement factors found in plasma. Because of these problems, cyclodextrins in the prior art are used for solubilizing and stabilizing certain drugs before or during administration but are not suitable for carrying and delivering drugs in the bloodstream.

Others have disclosed the use of cyclodextrin polymers in chromatography and for complexing with a variety of substances. However, these compositions also suffer the same problem of loading by diffusion and uncontrolled release by diffusion, which is unsuitable when such preparations are diluted as through administration into the bloodstream. The cyclodextrin polymer carriers of the instant invention overcome these problems and provide the new function of controlled release for cyclodextrins, which is not disclosed or suggested by the prior art.

SUMMARY OF THE INVENTION

It has been discovered that the water soluble (or colloidal) cyclodextrin polymer carriers of the instant invention overcome the problems with individual cyclodextrins in the prior art. The instant invention provides new properties and unexpected advantages. In its simplest form, a cyclodextrin polymer carrier comprises a cyclodextrin polymer that has a drug or other active agent completely entrapped within it.

In one embodiment, the water soluble (or colloidal) cyclodextrin polymers of instant invention overcome the problem of low carrying capacity of individual cyclodextrins. Also, by complete entrapment of the guest molecules, the problem of losing drug or other active agent by diffusion when diluted in vivo, is solved. In another embodiment, the invention also provides a means for controlled release of the entrapped drug in vivo.

In another embodiment, the invention also provides a means for targeting the cyclodextrin polymer carrier by coupling it to a biorecognition molecule. The polymer carrier also allows the coupling of several drug molecules at each coupling site on a biorecognition molecule, which was not possible in the prior art.

The advantages of the water soluble (or colloidal) cyclodextrin polymer carrier are:

(1) Drugs can be used that are designed for efficacy without conjugation requirements.

(2) It will allow the use of drugs designed solely for efficacy without regard for solubility.

(3) Unmodified drugs can be delivered as macromolecules and released within the cell.

(4) Drugs can be targeted by coupling the carrier to biorecognition molecules.

(5) Synthesis methods are independent of the drug to facilitate multiple drug therapies.

These are new advantages and functions provided for anti-cancer and other drug carrier technology that will also be useful for other drug delivery applications. These compositions and methods are unanticipated or suggested in the prior art.

DETAILED DESCRIPTION OF THE INVENTION

For the purposes of disclosing this invention, certain words, phrases and terms used herein are defined as follows:

Active Agents

Active agents function as the preferred guest molecules of the instant invention. Active agents that are preferred in the instant invention are chemicals and other substances can form an inclusion complex with a cyclodextrin or cyclodextrin polymer and are inhibitory, antimetabolic or preventive toward any disease (i.e. cancer, syphilis, gonorrhea, influenza and heart disease) or inhibitory or toxic toward any disease causing agent. Preferred active agents are any therapeutic drugs categorized in The Merck Index, Eleventh Ed., Merck & Co. Inc., Rahway, N.J. (1989) and those listed by Cserhati, T., Anal.Biochem. 225(2), 328–332 (1995).

Active agents include any drugs including anticancer drugs, antineoplastic drugs, antifungal drugs, antibacterial drugs, antiviral drugs, cardiac drugs, neurological drugs, and drugs of abuse; alkaloids (i.e. camptothecins), antibiotics, bioactive peptides, steroids, steroid hormones, polypeptide hormones, interferons, interleukins, narcotics, nucleic acids including antisense oligonucleotides, pesticides and prostaglandins.

Active agents also include any toxins including aflatoxins, ricins, bungarotoxins, irinotecan, ganciclovir, furosemide, indomethacin, chlorpromazine, methotrexate, cevine derivatives and analogs including cevadines, desatrines, veratridine, among others.

Also included are;

various flavone derivatives and analogs including dihydroxyflavones (chrysins), trihydroxyflavones (apigenins), pentahydroxyflavones (morins), hexahydroxyflavones (myricetins), flavyliums, quercetins, fisetins;

various antibiotics including penicillin derivatives (i.e. ampicillin), anthracyclines (i.e. doxorubicin, daunorubicin), teramycins, tetracyclines, chlorotetracyclines, clomocyclines, butoconazole, ellipticines, guamecyclines, macrolides (i.e. amphotericins), filipins, fungichromins, nystatins;

various purine and pyrimidine derivatives and analogs including 5'-fluorouracil, 5'-fluoro-2'-deoxyuridine, and allopurinol;

various photosensitizer substances, especially those used for singlet and triplet oxygen formation useful for photodynamic therapy (van Lier, J. E. In "Photodynamic Therapy of Neoplastic Disease"; Kessel, D., Ed., CRC Press, Boca Raton, Fla., 1990, Vol. I), including meso-chlorin $e_6$ monoethylenediamine ($Mce_6$), phytalocyanine, porphyrins and their derivatives and analogs;

various steroid derivatives and analogs including cholesterols, digoxigenins; various coumarin derivatives and analogs including dihydroxycoumarins (esculetins), dicumarols; chrysarobins, chrysophanic acids, emodins, secalonic acids;

various dopas, derivatives and analogs including dopas, dopamines, epinephrines, and norepinephrines (arterenols).

Other specific active agents are anti-viral drugs, nucleic acids and other anti-viral substances including those against any DNA and RNA viruses, AIDS, HIV and hepatitis viruses, adenoviruses, alphaviruses, arenaviruses, coronaviruses, flaviviruses, herpesviruses, myxoviruses, oncornaviruses, papovaviruses, paramyxoviruses, parvoviruses, picornaviruses, poxviruses, reoviruses, rhabdoviruses, rhinoviruses, togaviruses and viriods; any anti-bacterial drugs, nucleic acids and other anti-bacterial substances including those against gram-negative and gram-positive bacteria, acinetobacter, achromobacter, bacteroides, clostridium, chlamydia, enterobacteria, haemophilus, lactobacillus, neisseria, staphyloccus, and streptoccocus; any anti-fungal drugs, nucleic acids and other anti-fungal substances including those against aspergillus, candida, coccidiodes, mycoses, phycomycetes, and yeasts; any drugs, nucleic acids and other substances against mycoplasma and rickettsia; any anti-protozoan drugs, nucleic acids and other substances; any anti-parasitic drugs, nucleic acids and other substances; any drugs, nucleic acids and other substances against heart diseases, tumors, and virus infected cells, among others.

Biocleavable Linkage or Bond

For the instant invention, biocleavable linkages are defined as types of specific chemical moieties or groups used within the chemical substances that covalently couple and cross-link the cyclodextrin polymer carriers. They are contained in certain embodiments of the instant invention that provide the function of controlled release of an entrapped drug or other active agent. Biocleavable linkages or bonds are defined here under two distinct categories or types.

One category comprises the disulfide linkages and ester bonds that are well known for covalent coupling drugs to polymers. However, for the purpose of drug delivery, they have limited value in vivo since they can be cleaved in the bloodstream relatively easily.

Another category comprises linkages or bonds that are more specifically cleaved after entering the cell (intracellular cleavage). The preferred linkages for release of drugs within the cell are cleavable in acidic conditions like those found in lysosomes. One example is an acid-sensitive (or acid-labile) hydrazone linkage as described by Greenfield, et al, Cancer Res. 50, 6600–6607 (1990), and references therein. Also preferred are certain natural or synthetic polypeptides that contain certain amino acid sequences (i.e. are hydrophobic) that are cleaved by specific enzymes such as cathepsins, found primarily inside the cell. Using the convention of starting with the amino or "N" terminus on the left and the carboxyl or "C" terminus on the right, some examples are: Gly-Phe-Leu-Gly, and Gly-Phe-Phe-Gly, among others.

Another preferred type of biocleavable linkage is any "hindered" or "protected" disulfide bond that sterically inhibits attack from thiolate ions. Examples of such protected disulfide bonds are found in the coupling agents: S-4-succinimidyloxycarbonyl-α-methyl benzyl thiosulfate (SMBT) and 4-succinimidyloxycarbonyl-α-methyl-α-(2-pyridyldithio) toluene (SMPT).

Biorecognition Molecules

For the purposes of this invention, biorecognition molecules function as those that bind to a specific biological substance or site. The biological substance or site is considered the "target" of the biorecognition molecule that binds to it. In the prior art, many drugs are "targeted" by coupling them to a biorecognition molecule that has a specific binding affinity for the cells, tissue or organism that the drug is intended for. For targeting a drug or other active agent in this invention, a biorecognition molecule is coupled to a cyclodextrin polymer carrier that has the drug or active agent entrapped within. Examples of biorecognition molecules are described below.

Ligand

A ligand functions as a type of biorecognition molecule defined as a selectively bindable material that has a selective (or specific), affinity for another substance. The ligand is recognized and bound by a usually, but not necessarily, larger specific binding body or "binding partner", or "receptor". Examples of ligands suitable for targeting are antigens, haptens, biotin, biotin derivatives, lectins, galactosamine and fucosylamine moieties, receptors, substrates, coenzymes and cofactors among others.

When applied to the cyclodextrin polymers of this invention, a ligand includes an antigen or hapten that is capable of being bound by, or to, its corresponding antibody or fraction thereof. Also included are viral antigens or hemagglutinins and neuraminidases and nucleocapsids including those from any DNA and RNA viruses, AIDS, HIV and hepatitis viruses, adenoviruses, alphaviruses, arenaviruses, coronaviruses, flaviviruses, herpesviruses, myxoviruses, oncornaviruses, papovaviruses, paramyxoviruses, parvoviruses, picornaviruses, poxviruses, reoviruses, rhabdoviruses, rhinoviruses, togaviruses and viriods; any bacterial antigens including those of gram-negative and gram-positive bacteria, acinetobacter, achromobacter, bacteroides, clostridium, chlamydia, enterobacteria, haemophilus, lactobacillus, neisseria, staphyloccus, and streptoccocus; any fungal antigens including those of aspergillus, candida, coccidiodes, mycoses, phycomycetes, and yeasts; any mycoplasma antigens; any rickettsial antigens; any protozoan antigens; any parasite antigens; any human antigens including those of blood cells, virus infected cells, genetic markers, heart diseases, oncoproteins, plasma proteins, complement factors, rheumatoid factors. Included are cancer and tumor antigens such as alpha-fetoproteins, prostate specific antigen (PSA) and CEA, cancer markers and oncoproteins, among others.

Other substances that can function as ligands are certain proteins, histones, hormones, vitamins, steroids, prostaglandins, synthetic or natural polypeptides, carbohydrates, lipids, antibiotics, drugs, digoxins, pesticides, narcotics, neuro-transmitters, and substances used or modified such that they function as ligands. Ligands also include various substances with selective affinity for ligators that are produced through recombinant DNA, genetic and molecular engineering. Except when stated otherwise, ligands of the instant invention also include the ligands as defined by K. E. Rubenstein, et al, U.S. Pat. No. 3,817,837 (1974).

Ligator

A ligator functions as a type of biorecognition molecule defined for this invention as a specific binding body or "partner" or "receptor", that is usually, but not necessarily, larger than the ligand it can bind to. For the purposes of this invention, it is a specific substance or material or chemical or "reactant" that is capable of selective affinity binding with a specific ligand. A ligator can be a protein such as an antibody, a nonprotein binding body or a "specific reactor."

When applied to this invention, a ligator includes an antibody, which is defined to include all classes of antibodies, monoclonal antibodies, chimeric antibodies, Fab fractions, fragments and derivatives thereof. Under certain conditions, the instant invention is also applicable to using other substances as ligators. For instance, other ligators suitable for targeting include naturally occurring receptors, any hemagglutinins and cell membrane and nuclear derivatives that bind specifically to hormones, vitamins, drugs, antibiotics, cancer markers, genetic markers, viruses, and histocompatibility markers. Another group of ligators includes any RNA and DNA binding proteins.

Other ligators also include enzymes, especially cell surface enzymes such as neuraminidases, plasma proteins, avidins, streptavidins, chalones, cavitands, thyroglobulin, intrinsic factor, globulins, chelators, surfactants, organometallic substances, staphylococcal protein A, protein G, ribosomes, bacteriophages, cytochromes, lectins, certain resins, and organic polymers. Ligators also include various substances such as any proteins with selective affinity for ligands that are produced through recombinant DNA, genetic and molecular engineering.

Nucleic Acid

For the purposes of this invention, certain nucleic acids can function as biorecognition molecules. A nucleic acid is defined as any nucleic acid sequence from any source. The nucleic acid includes all types of RNA, all types of DNA, and oligonucleotides including probes and primers used in the polymerase chain reaction (PCR) or DNA sequencing, antisense oligonucleotides and phosphorthioate oligonucleotides. Also included are synthetic nucleic acid polymers and peptide nucleic acids (PNA) disclosed by Egholm, et al, Nature 365:566–568(1993) and references therein, including PNA clamps (Nucleic Acids Res. 23:217(1995)). Also included are DNA and/or RNA fragments, and derivatives from any tissue, cells, nuclei, chromosomes, cytoplasm, mitochondria, ribosomes, and other cellular sources.

Cyclodextrin

A cyclodextrin (CD), is an oligosaccharide composed of glucose monomers coupled together to form a conical, hollow molecule with a hydrophobic interior or cavity. The cyclodextrins of the instant invention can be any suitable cyclodextrin, including alpha-, beta-, and gamma-cyclodextrins, and their combinations, analogs, isomers, and derivatives. They function as components in the synthesis of the cyclodextrin polymer carriers of the instant invention.

In describing this invention, references to a cyclodextrin "complex", means a noncovalent inclusion complex. An inclusion complex is defined herein as a cyclodextrin functioning as a "host" molecule, combined with one or more "guest" molecules that are contained or bound, wholly or partially, within the hydrophobic cavity of the cyclodextrin or its derivative.

Most preferred are derivatives such as carboxymethyl CD, glucosyl CD, maltosyl CD, hydroxypropyl cyclodextrins (HPCD), 2-hydroxypropyl cyclodextrins, 2,3-dihydroxypropyl cyclodextrins (DHPCD), sulfobutylether CD, ethylated and methylated cyclodextrins. Also preferred are oxidized cyclodextrins that provide aldehydes and any oxidized forms of any derivatives that provide aldehydes. Some examples of suitable derivatives are disclosed by Pitha, J., et al, J. Pharm. Sci. 75, 165–167 (1986) and Pitha, J., et al, Int. J. Pharmaceut. 29, 73–82 (1986).

Also included are altered forms, such as crown ether-like compounds prepared by Kandra, L., et al, J. Inclus. Phenom. 2, 869–875 (1984), and higher homologues of cyclodextrins, such as those prepared by Pulley, et al, Biochem. Biophys. Res. Comm. 5, 11 (1961). Some useful reviews on cyclodextrins are: Atwood J. E. D., et al, Eds., "Inclusion Compounds", vols. 2 & 3, Academic Press, NY (1984); Bender, M. L., et al, "Cyclodextrin Chemistry", Springer-Verlag, Berlin, (1978) and Szejtli, J., "Cyclodextrins and Their Inclusion Complexes", Akademiai Kiado, Budapest, Hungary (1982). These references, including references contained therein, are applicable to the synthesis of the preparations and components of the instant invention and are hereby incorporated herein by reference.

Cyclodextrin Dimers, Trimers and Polymers

For this invention, individual cyclodextrin derivatives as well as dimers, trimers and polymers function as the primary structures, or components, or units (i.e. monomer) used to synthesize the water soluble (or colloidal) cyclodextrin polymer carriers. A cyclodextrin dimer is defined as a unit of two cyclodextrin molecules covalently coupled or cross-linked together to enable cooperative complexing with a guest molecule. Examples of some CD dimers that can be used to synthesize the CD polymer carriers of this invention, are described by; Breslow, R., et al, Amer. Chem. Soc. 111, 8296–8297 (1989); Breslow, R., et al, Amer. Chem. Soc. 105, 1390 (1983) and Fujita, K., et al, J. Chem. Soc., Chem. Commun., 1277 (1984).

A cyclodextrin trimer is defined as a unit of three cyclodextrin molecules covalently coupled or cross-linked together to enable cooperative complexing with a guest molecule. A cyclodextrin polymer is defined as a unit of more than three cyclodextrin molecules covalently coupled or cross-linked together to enable cooperative complexing with several guest molecules.

For this invention, preferred cyclodextrin dimer, trimer and polymer units are synthesized by covalently coupling through chemical groups such as coupling agents not to exceed 50 angstroms in spacer length. The synthesis of preferred cyclodextrin dimer, trimer and polymer units does not include the use of proteins or other "intermediate coupling substances" (defined below), which can be incorporated during final synthesis of the cyclodextrin polymer carrier. Cooperative complexing means that in situations where the guest molecule is large enough, the member cyclodextrins of the CD dimer, trimer or polymer can each noncovalently complex with different parts of the same guest molecule, or with smaller guests, alternately complex with the same guest.

The prior art has disclosed dimers and polymers comprised of cyclodextrins of the same size. An improved cyclodextrin dimer, trimer or polymer comprises combinations of different sized cyclodextrins to synthesize these units. These combinations may more effectively complex with guest molecules that have heterogeneous complexing sites. Combinations for this invention can include the covalent coupling of an alpha CD with a beta CD, an alpha CD with a gamma CD, a beta CD with a gamma CD and polymers with various ratios of alpha, beta and gamma cyclodextrins.

Cyclodextrin Polymer Carrier

A water soluble (or colloidal) cyclodextrin polymer carrier is a new composition provided by the instant invention. It is defined herein as a polymer of cross-linked cyclodextrin derivatives that has the distinguishing property of having incorporated a drug or other active agent as a "captured guest". The "capture" of the guest stabilizes the carrier complex and overcomes the problem in the prior art of the CD host and guest molecules separating by diffusion. Generally, the agent has also formed a noncovalent "inclusion complex", or "inclusion compound" with the cyclodextrins of the polymer.

Captured Guest Cyclodextrin Polymer Carrier

In one embodiment the captured guest molecule is covalently tethered through a spacer to the water soluble (or colloidal) CD polymer to allow formation of a noncovalent complex between the guest and the host CD within the polymer. Cyclodextrin molecules have their functional groups only on the periphery so that the interior is nonreactive. Therefore, in this embodiment, the guest molecule can form a noncovalent inclusion complex within the cyclodextrin polymer host even though the captured guest is covalently tethered to the host periphery.

In another preferred embodiment the capturing is accomplished through complete physical entrapment by the water soluble (or colloidal) CD polymer carrier. In this embodiment, "completely entrapped" means that a captured guest is not covalently coupled to the polymer but is entrapped within the covalently cross-linked polymer of cyclodextrin molecules so that it cannot leave the polymer by diffusion or extraction. Completely entrapped guests cannot escape until the polymer itself has been degraded or the covalent cross-link bonds are cleaved. In this embodiment, essentially all possible exit routes for the guest to leave the polymer have been closed by cross-linking. Therefore, additional guest molecules (of that size or larger), cannot enter the closed polymer to be added to the cyclodextrin polymer carrier.

This is made possible through the unique method for synthesizing the cyclodextrin polymer carriers of the instant invention. The distinguishing principal of the method is that the guest molecules are completely entrapped during polymerization or during the final cross-linking step of making the polymer carrier. Initially, guest molecules are mixed with the "open" components of the cyclodextrin polymer, which may comprise individual cyclodextrins (or derivatives), cyclodextrin dimers, trimers or an open cyclodextrin polymer. An open cyclodextrin polymer means that the polymer is only partially cross-linked so that guest molecules can enter the polymer by diffusion and form complexes with member cyclodextrins. In the final synthesis step of the polymer carrier, the polymer is closed by additional cross-linking which completely entraps the guests.

Controlled Release

For this invention, controlled release is defined as the release of a captured guest from the CD polymer carrier only by cleavage of certain linkages that were used to synthesize the carrier. This definition specifically excludes release by diffusion until said linkages are cleaved.

Targeted Cyclodextrin Polymer Carriers

A targeted cyclodextrin (CD) polymer carrier is an embodiment of this invention composed of a water soluble (or colloidal) cyclodextrin polymer carrier, or derivative described herein, that has a biorecognition molecule covalently coupled to its surface. However, the biorecognition molecule is not an inclusion complex within the cyclodextrin carrier. The carrier is thereby targeted through the specific binding properties of the biorecognition molecule coupled to the surface.

During the coupling, the functions of the biorecognition molecule and the targeted CD polymer carrier are not irreversibly or adversely inhibited. Preferably, the biorecognition molecule maintains specific binding properties that are functionally identical or homologous to those it had before coupling. Preferably, the biorecognition molecule is coupled through a suitable spacer to avoid steric hindrance.

Targeted cyclodextrin polymer carriers coupled to avidin and streptavidin are useful for subsequent noncovalent coupling to any suitable biotinylated substance. Similarly, cyclodextrin polymer carriers coupled to antibody can be noncovalently coupled to another antibody, or to a nucleic acid or other suitable substance that has the appropriate biorecognition properties. Another useful cyclodextrin carrier comprises protein A, protein G, or any suitable lectin or polypeptide that has been covalently coupled to a cyclodextrin polymer carrier.

Biocleavable Cross-Linking Agent

A biocleavable cross-linking agent comprises a new invention for facilitating the synthesis of drug carriers with controlled release. In one embodiment it is comprised of a biocleavable sequence of amino acids that has amino groups at each end for direct coupling to amino-reactive coupling agents. Using the convention of starting with the amino or "N" terminus on the left and the carboxyl or "C" terminus on the right, some examples are: Gly-Phe-Leu-Gly-Lys, or Lys-Gly-Phe-Leu-Gly-Lys. Another embodiment comprises a synthetic polypeptide with a biocleavable sequence as described, and also includes N-succinimidyl, or N-maleimydyl, or imidoester coupling groups on each end.

For acid-labile biocleavable cross-linking agents, one embodiment comprises a bifunctional coupling agent with a hydrazone linkage incorporated into it. For instance, it would comprise a hydrazone linkage between aliphatic chains that have N-succinimidyl, or N-maleimydyl, or imidoester coupling groups on each end. One example for synthesizing an acid-labile biocleavable coupling agent is to first react an excess of hydrazinobenzoic acid with glutaraldehyde to couple one hydrazinobenzoic acid at each end of the dialdehyde. This produces hydrazone linkages with terminal carboxyl groups at each end. The terminal carboxyl groups are then converted to N-succinimidyl ester groups.

Coupling

For the instant invention, two distinct types of coupling are defined. One type of coupling can be through noncovalent, "attractive" binding as with a guest molecule and cyclodextrin, antigen and antibody or biotin and avidin. Noncovalent coupling is binding between substances through ionic or hydrogen bonding or van der waals forces, and/or their hydrophobic or hydrophilic properties.

Unless stated otherwise, the preferred coupling used in the instant invention is through covalent, electron-pair bonds. Many methods and agents for covalently coupling (or crosslinking) cyclodextrins and cyclodextrin derivatives are known and, with appropriate modification, can be used to couple the desired substances through their "functional groups" for use in this invention.

Functional Group

A functional group is defined here as a potentially reactive site on a substance where one or more atoms are available for covalent coupling to some other substance. When needed, functional groups can be added to various substances through derivatization or substitution reactions.

Examples of functional groups are aldehydes, allyls, amines, amides, azides, carboxyls, carbonyls, epoxys, ethynyls, hydroxyls, ketones, metals, nitrenes, phosphates, propargyls, sulfhydryls, sulfonyls, thioethers, phenolic hydroxyls, indoles, bromines, chlorines, iodines, and others. The prior art has shown that most, if not all of these functional groups can be incorporated into or added to cyclodextrins, biorecognition molecules, nucleic acids and support materials.

Cross-Linking or Coupling Agent

A coupling agent (or cross-linking agent), is defined as a chemical substance that produces and/or reacts with functional groups on a substance to produce covalent coupling, cross-linking, or conjugation with that substance. Because of the stability of covalent coupling, this is the preferred method. Depending on the chemical makeup or functional group on the cyclodextrin, nucleic acid, or biorecognition molecule, the appropriate coupling agent is used to provide the necessary active functional group or to react with the functional group. In certain preparations of the instant invention, coupling agents are needed that provide a spacer between cross-linked cyclodextrins or between cyclodextrin and a biorecognition molecule to overcome steric hindrance. Preferably, the spacer is a substance of 4 or more carbon atoms in length and can include aliphatic, aromatic and heterocyclic structures.

With appropriate modifications by one skilled in the art, the coupling methods referenced below, including references contained therein, are applicable to the synthesis of the preparations and components of the instant invention and are hereby incorporated by reference, herein:

Blair, A. H., et al, J. Immunol. Methods 59, 129–143 (1983);

Erlanger, B. F., Pharmacol. Rev. 25, 271–280 (1973);

Kenyon, G. L., et al, "Novel Sulfhydryl Reagents", Meth. in Enzym. 47, 407–430 (1977);

Mather, N. K., et al, Eds., "Polymers as Aids in Organic Chemistry", Chapter 2, Academic Press, N.Y. (1980); and O'Carra, P., et al, FEBS Lett. 43, 169–175 (1974).

Examples of energy activated coupling or cross-linking agents are ultraviolet (UV), visible and radioactive radiation that can promote coupling or crosslinking of suitably derivatized cyclodextrins. Examples are photochemical coupling agents disclosed in U.S. Pat. No. 4,737,454, among others. Also useful in synthesizing components of the instant invention are enzymes that produce covalent coupling such as nucleic acid polymerases and ligases, among others.

Most preferred coupling agents are chemical substances, that can provide the bio-compatible linkages for synthesizing the water soluble cyclodextrin polymer carriers of the instant invention. Covalent coupling or conjugation can be done through functional groups using coupling agents such as glutaraldehyde, formaldehyde, cyanogen bromide, azides, p-benzoquinone, succinic anhydrides, carbodiimides, maleimides, epichlorohydrin, periodic acid, ethyl chloroformate, dipyridyl disulfide and polyaldehydes.

Other coupling agents useful in the instant invention are:
bifunctional imidoesters such as dimethyl adipimidate (DMA), dimethyl pimelimidate (DMP), dimethyl suberimidate (DMS), dimethyl 3,3'-dithiobis-propionimidate (DTBP), and 2-iminothiolane (Traut's reagent);

bifunctional NHS esters such as disuccinimidyl suberate (DSS), bis[2-(succinimidooxycarbonyloxy)ethyl]sulfone (BSOCOES), disuccinimidyl (N,N'-diacetylhomocystein) (DSAH), disuccinimidyl tartrate (DST), dithiobis (succinimidyl propionate) (DSP), and ethylene glycol bis (succinimidyl succinate) (EGS), including various derivatives such as their sulfo- forms;

heterobifunctional reagents such as N-5-azido-2-nitrobenzoyloxysuccinimide (ANB-NOS), p-azidophenacyl bromide, p-azidophenylglyoxal, 4-fluoro-3-nitrophenyl azide (FNPA), N-hydroxysuccinimidyl-4-azidobenzoate (HSAB), m-maleimidobenzoyl-N-hydroxysuccinimide ester (MBS), methyl-4-azidobenzoimidate (MABI), p-nitrophenyl 2-diazo-3,3,3-trifluoropropionate, N-succinimidyl-6(4'-azido-2'-nitrophenylamino) hexanoate (Lomant's reagent II), succinimidyl 4-(N-maleimidomethyl) cyclohexane-1-carboxylate (SMCC), succinimidyl 4-(p-maleimidophenyl)butyrate (SMPB), N-succinimidyl (4-azidophenyldithio)propionate (SADP), N-succinimidyl-3-(2-pyridyldithio)propionate (SPDP), and N-(4-azidophenylthio)phthalimide (APTP), including various derivatives such as their sulfo- forms;

homobifunctional reagents such as 1,5-difluoro-2,4-dinitrobenzene, 4,4'-difluoro-3,3'-dinitrophenylsulfone, 4,4'-diisothiocyano-2,2'-disulfonic acid stilbene (DIDS), p-phenylenediisothiocyanate (DITC), carbonylbis(L-methionine p-nitrophenyl ester), 4,4'-dithiobisphenylazide and erythritolbiscarbonate, including various derivatives such as their sulfo- forms;

photoactive coupling agents such as N-5-azido-2-nitrobenzoylsuccinimide (ANB-NOS), p-azidophenacyl bromide (APB), p-azidophenyl glyoxal (APG), N-(4-azidophenylthio)phthalimide (APTP), 4,4'-dithio-bis-phenylazide (DTBPA), ethyl 4-azidophenyl-1,4-dithiobutyrimidate (EADB), 4-fluoro-3-nitrophenyl azide (FNPA), N-hydroxysuccinimidyl-4azidobenzoate (HSAB), N-hydroxysuccinimidyl-4-azidosalicylic acid (NHS-ASA), methyl-4-azidobenzoimidate (MABI), p-nitrophenyl-2-diazo-3,3,3-trifluoropropionate (PNP-DTP), 2-diazo-3,3,3-trifluoropropionyl chloride, N-succinimidyl-6(4'-azido-2'-nitrophenylamino)hexanoate (SANPAH), N-succinimidyl (4-azidophenyl)1,3'-dithiopropionate (SADP), sulfosuccinimidyl-2-(m-azido-o-nitobenzamido)-ethyl-1,3'-dithiopropionate (SAND), sulfosuccinimidyl(4-azidophenyldithio)propionate (Sulfo-SADP), sulfosuccinimidyl-6-(4'-azido-2'-nitrophenylamino) hexanoate (Sulfo-SANPAH), sulfosuccinimidyl-2-(p-azidosalicylamido)ethyl-1,3'-dithiopropionate (SASD), and derivatives and analogs of these reagents, among others. The structures and references for use are given for many of these reagents in, "Pierce Handbook and General Catalog", Pierce Chemical Co., Rockford, Ill., 61105.

Intermediate Coupling Substance

In addition to covalently coupling directly through functional groups of cyclodextrin derivatives to synthesize water soluble (or colloidal) polymers, it is also useful to include an intermediate substance or "intermediate". By definition, intermediate substances function as bio-compatible intermediates in being nonimmunogenic and nonallergenic. Although intermediate substances may be degraded biologically, they are "biologically neutral" in that they lack specific binding properties or biorecognition properties.

The intermediate can function as a "spacer" (e.g. "spacer arm" of O'Carra, supra), between the cyclodextrin derivatives being covalently coupled to overcome steric hindrance of subsequent binding reactions. The intermediate can function as a polymer "backbone" to which many cyclodextrin dimers, trimers or polymers are covalently coupled to form a larger polymer. The intermediate can be included with cyclodextrin derivatives as another monomer to be copolymerized with the cyclodextrin derivatives (i.e. heteropolymer), to provide improved structural properties, increase solubility or lower toxicity.

The intermediate substance may also provide the advantage of additional coupling sites and thereby increase the number of covalently coupled cyclodextrin derivatives within a polymer carrier. The intermediate can also introduce certain other desirable properties, such as more efficient light energy transfer for photodynamic therapy. The desired biorecognition molecule or other substance, can be coupled to the available sites on the intermediate substance and is thereby coupled indirectly to the water soluble cyclodextrin polymer carrier of the instant invention.

Examples of such biologically neutral intermediate coupling substances are certain proteins, polypeptides, polyamino acids, glycoproteins, lipoproteins, nucleic acid polymers, DNA, RNA, amino sugars, glucosamines, polysaccharides, lipopolysaccharides, amino polysaccharides, polyglutamic acids, polylysines, polyacrylamides, nylons, poly(allylamines), lipids, glycolipids and suitable synthetic polymers, especially biopolymers, resins and surfactants, as well as suitable derivatives of these substances. Also included as suitable intermediate coupling substances are the polymers disclosed in U.S. Pat. No. 4,645,646. Also included as intermediates are N-(2-hydroxypropyl)methacrylamide (HPMA), and HPMA derivatives, and poly (D,L-lactide)-block-methoxypolyethylene glycol (Diblock).

Various materials may be incorporated into the components of the instant invention to produce new inventions with unexpected properties for use in certain applications. For instance, the addition of ferrous or magnetic particles may be used to give cyclodextrin polymer carriers and other types of polymers (i.e. HPMA), magnetic properties (Ithakissios, D. S., Clin. Chim. Acta 84(1–2), 69–84, 1978). This would be useful for various in vivo manipulations such as using magnetic fields to localize or concentrate a magnetic polymer drug carrier in a specific part of the body. Also, the magnetic particles may be used to trigger a cytotoxic effect on cancer cells such as by vibrating them with alternating magnetic fields.

EXAMPLES

In the examples to follow, percentages are by weight unless indicated otherwise. During the synthesis of the compositions of the instant invention, it will be understood by those skilled in the art of organic synthesis methods, that there are certain limitations and conditions as to what compositions will comprise a suitable carrier. It will be understood in the art of cyclodextrins that there are limitations as to which drugs and other agents can be used to form inclusion complexes with certain cyclodextrins.

Specifically, it is known that smaller, alpha cyclodextrins are preferably used to complex with the smaller drugs or active agents. Whereas larger cyclodextrins are less limited, except that a "close fit" is generally preferred for stronger complexing affinity.

The terms "suitable" and "appropriate" refer to synthesis methods known to those skilled in the art that are needed to perform the described reaction or procedure. In the references to follow, the methods are hereby incorporated herein by reference. For example, organic synthesis reactions, including cited references therein, that can be useful in the instant invention are described in "The Merck Index", 9, pages ONR-1 to ONR-98, Merck & Co., Rahway, N.J. (1976), and suitable protective methods are described by T. W. Greene, "Protective Groups in Organic Synthesis", Wiley-Interscience, NY (1981), among others. For synthesis of nucleic acid probes, sequencing and hybridization methods, see "Molecular Cloning", 2nd edition, T. Maniatis, et al, Eds., Cold Spring Harbor Lab., Cold Spring Harbor, N.Y. (1989).

All reagents and substances listed, unless noted otherwise, are commercially available from Aldrich Chemical Co., WI 53233; Sigma Chemical Co., Mo. 63178; Pierce Chemical Co., IL. 61105; Eastman Kodak Co., Rochester, N.Y.; Pharmatec Inc., Alachua, Fla. 32615; and Research Organics, Cleveland, Ohio. Or, the substances are available or can be synthesized through referenced methods, including "The Merck Index", 9, Merck & Co., Rahway, N.J. (1976).

Additional references cited are hereby incorporated herein by reference.

Buckler, et al, U.S. Pat. No. 4,331,808 (1982),

Langer, P. R., et al, Proc. Natl. Acad. Sci. USA 78, 6633–6637 (1981)

Patel, A., et al, Clin. Chem. 29/9, 1604–1608 (1983),

Roswell, D. F., et al, J. Amer. Chem. Soc. 92, 4855–4860 (1970),

Roberts, D. R., et al, J. Amer. Chem. Soc. 92, 4861–4867 (1970),

Robins, M. J., et al, Can. J. Chem. 60, 554–557 (1981)

Sessler, J. L., et al, J. Inclus. Phenom. Mol. Recog. Chem. 7, 19–26 (1989)

Theodoropulos, S. U.S. Pat. No. 4,600,775 (1986),

Wei, C. C., et al, Tetrahedron Lett., No. 39, 3559–3562 (1971),

White, E. H., et al, Accounts Chem. Res. 3, 54 (1970)

White, E. H., et al, J. Organ. Chem. 32, 1198 (1967),

White, E. H., et al, J. Amer. Chem. Soc. 89, 3944 (1967).

CYCLODEXTRIN POLYMER CARRIERS

The purpose is to provide a water soluble (or colloidal) cyclodextrin polymer carrier that has an active agent completely entrapped within. For synthesis, the general approach is; (1) to produce or modify or protect, as needed, one or more functional or coupling groups on the cyclodextrin components, consisting of cyclodextrins, or open dimers, trimers or polymers; (2) combine under appropriate conditions, a minimum of 4 of the cyclodextrin components with a drug or active agent to produce a noncovalent inclusion complex and (3) using various coupling methods cross-link the cyclodextrin components to produce a polymer that completely entraps the drug within the cyclodextrin polymer.

Also, as described below, the cyclodextrin polymer carrier may be suitably derivatized to include other useful substances and/or chemical groups (e.g. biorecognition molecules, antenna, and catalytic substances), to perform a particular function. Depending on the requirements for chemical synthesis, the derivatization can be done before entrapment or afterward, using suitable protection and deprotection methods as needed.

Since cyclodextrins are composed of carbohydrates, they can be suitably derivatized and coupled through well-known procedures used for other carbohydrates, especially through available hydroxyl groups. For instance, vicinal hydroxyl groups on the cyclodextrin can be appropriately oxidized to produce aldehydes.

In addition, any functional group can be suitably added through well-known methods while preserving the cyclodextrin structure and complexing properties. Examples are: amidation, esterification, acylation, N-alkylation, allylation, ethynylation, oxidation, halogenation, hydrolysis, reactions with anhydrides, or hydrazines and other amines, including the formation of acetals, aldehydes, amides, imides, carbonyls, esters, isopropylidenes, nitrenes, osazones, oximes, propargyls, sulfonates, sulfonyls, sulfonamides, nitrates, carbonates, metal salts, hydrazones, glycosones, mercaptals, and suitable combinations of these. The functional groups are then available for the cross-linking of one or more cyclodextrin molecules using a bifunctional reagent.

Additional examples of cyclodextrins, inclusion compounds and catalytic groups including chemical methods for modifying and/or derivatizing cyclodextrins that are useful in the instant invention are described in the following references, which are incorporated herein by reference.

Atwood J. E. D., et al, Eds., "Inclusion Compounds", vols. 2 & 3, Acad. Press, NY (1984)

Bender, M. L., et al, "Cyclodextrin Chemistry", Springer-Verlag, Berlin, (1978)

Baldwin, E., et al, Science 245, 1104–1107 (1989)

Bender, M. L., J. Inclus. Phenom. 2, 433–444 (1984)

Bergeron, R. J., et al, Bioorgan. Chem. 5, 121–126 (1976)

Boger, J., et al, Helvet. Chim. Acta 61, 2190–2218 (1978)

Breslow, R., et al, J. Amer. Chem. Soc. 92/4, 1075–1077 (1970)

Buckler, S. A., et al, U.S. Pat. No. 3,472,835 (1969)

Carlsson, J., et al, Eur. J. Biochem. 59, 567–572 (1975)

Case, L. C., U.S. Pat. Nos. 3,502,601 (1970) and 3,510, 471 (1970)

Cramer, F., et al, Chem. Ber. 103, 2138 (1970)

Cramer, F., et al, J. Amer. Chem. Soc. 89:1, 14–20 (1967)

Emert, J., et al, J. Amer. Chem. Soc. 97, 670 (1975)

Erlanger, B. F., Pharmacol. Rev. 25, 271–280 (1973)

Furue, M. A., et al, Polymer. Lett. 13, 357 (1975)

Gramera, R. E., et al, Fr. Demande 1, 584, 917 (1968)

Harada, A., et al, Macromolecules 9, 701 and 705 (1976)

Hatano, M., et al, Japan Kokai 77,71,583 (1977)

Hirai, H., J. Inclus. Phenom. 2, 455–466 (1984)

Ikeda, T., et al, J. Inclus. Phenom. 2, 669–674 (1984)

Ikeda, T., et al, J. Inclus. Phenom. 5, 93–98 (1987)

Iwakura, Y., et al, J. Amer. Chem. Soc. 97/15, 4432–4434 (1975)

Ji, T. H., Biochim. et Biophys. Acta. 559, 39–69 (1979)

Johnson, C. K. U.S. Pat. No. 3,654,261 (1972)

Kawaguchi, Y., et al, Anal. Chem. 55, 1852–1857 (1983)

Klotz, I. M., et al, Arch. Biochem. Biophys. 96, 605–612 (1961)

Kobayashi, M., et al, Agric. Biol. Chem. 52, 2695–2702 (1988).

Lui, F- T., et al, Biochem. 18, 690–697 (1979)

Matsui, Y., et al, Chem. Lett., Oct., 1037–1040 (1976)

Muller, B. W. W., et al U.S. Pat. No. 4,764,604 (1988)

Ogata, N., Japan Kokai 77,121,096 (1977)

Parmerter, S. M., U.S. Pat. Nos. 3,426,011 (1969) and 3,453,257 (1969)

Patonay, G., et al, Anal. Chem. 57, 569–571 (1985)

Royer, G. P., et al, Biochem. Biophys. Res. Comm. 64, 478–484 (1975)

Schultz, P. G., Science 240, 426 (1988)

Smolkova-Keulemansova, E., J. Chromatog. 251, 17–34 (1982)

Szejtli, J., "Cyclodextrins and Their Inclusion Complexes", A. Kiado, Budapest, Hungary (1982)

Szejtli, J., et al, Hung. Patent 19,626 (1978)

Tabushi, I., et al, J. Amer. Chem. Soc. 98/24, 7855–7856 (1976)

Tabushi, I., et al, Tetrahed. Lett. No. 29, 2503–2506 (1977)

Tabushi, I., Acc. Chem. Res. 15, 66–72 (1982)

Traut, R. R., et al, Biochem. 12, 3266–3273 (1973)

Tsuchiyama, Y., et al, U.S. Pat. No. 4,746,734 (1988)

Ueno, A., et al, J. Inclus. Phenom. 2, 555–563 (1984)

VanEtten, R. L., et al, J. Amer. Chem. Soc. 89/13 3242–3253 and 3253–3262 (1967)

Vretblad, P., FEBS Lett. 47, No. 1, 86–89, Oct., (1974)

Yagi, Y., et al, U.S. Pat. No. 4,781,977 (1988)

Suitable coupling or cross-linking agents for preparing the water soluble (or colloidal) CD carriers of the instant invention can be a variety of reagents previously described, including well known crosslinkers such as epichlorohydrin, isocyanates, and formaldehyde, used to polymerize CD's. Other suitable crosslinkers or derivatizers are various epoxy compounds including propylene oxide, 1,2-diethoxyethane, 1,2,7,8-diepoxyoctane, 2,3-epoxy-1-propanol (glycidol), glycerol propoxylate triglycidylether, 2,3-epoxy-1,4-butanediol, and 1,4-butanediol diglycidyl ether (e.g. Gramera, or Case, or Johnson, or Parmerter, supra). Also useful are methods employing acrylic esters such as m-nitrophenyl acrylates, and hexamethylenediamine and p-xylylenediamine complexes (e.g. Furue, or Harada, or Hatano, or Ogata, supra), and aldehydes, ketones, alkyl halides, acyl halides, silicon halides, isothiocyanates, and epoxides (e.g. Buckler, supra).

Methods for Derivatizing Cyclodextrins

For this invention, individual cyclodextrin derivatives as well as dimers, trimers and polymers are the primary components, or units (i.e. monomer) used to synthesize the water soluble (or colloidal) cyclodextrin polymer carriers. Although native cyclodextrins are useful for synthesizing the carriers, many other useful properties can be incorporated into the carriers by first derivatizing the cyclodextrin components before making the polymers. Derivatizing is defined as the chemical modification of a CD through addition of any functional or coupling group and/or other substance. Generally, derivatized cyclodextrins can be used to facilitate cross-linking reactions and introduce functional groups for use during or after the carrier is prepared. Frequently, an integral part of using derivatized cyclodextrins involves protecting certain functional groups during certain cross-linking steps and then deprotecting those groups for use in subsequent steps.

A. Protected Hydroxyl Groups

Primary and/or secondary hydroxyl groups on the cyclodextrin (or derivatives), can be selectively protected and deprotected using known methods during derivatizing and/or capping procedures, to provide selective coupling at the primary or secondary end of the CD molecule, as desired. For instance, formation of protective esters (e.g. benzoates using benzoyl chloride), and selective cleavage (deprotection), of primary esters using anhydrous alcoholysis (e.g. Boyer, supra), provides mostly primary hydroxyls for derivatization. After derivatization and/or coupling the primary hydroxyls, the secondary hydroxyls can be deprotected for additional derivatization, coupling and/or capping.

B. Preparation of Sulfonylated Cyclodextrin

A variety of suitable methods are available for sulfonylation of CD or CD polymer before or after protection of specific hydroxyl groups (e.g. Bergeron, Boger or Ueno, supra), and/or capping of the CD (e.g. Emert or Tabushi, supra). Suitably, CD polymer (10 gm), is combined with a suitable sulfonylating reagent (20 gm), such as p-toluenesulfonyl (tosyl) chloride, mesitylenesulfonyl chloride or naphthalenesulfonyl chloride, among others, in anhydrous pyridine, for 3–5 Hrs at room temperature (RT).

C. Preparation of Dialdehyde Cyclodextrin (Dial-CD)

A dialdehyde CD derivative (dial-CD) and dialdehyde cyclodextrin polymer (dial-CD polymer) is prepared by oxidation using known methods (e.g. Royer or Kobayashii, supra), with sodium metaperiodate in suitable buffer solution (e.g. 0.2 M phosphate saline, pH 5–7). For use in preparing cyclodextrin polymer carriers, dial-CD can also include oxidized forms of HPCD and DHPCD.

D. Amino-Cyclodextrin (Amino-CD) Derivatives

Amino groups can be introduced into CD polymer by reaction of a sulfonylated CD polymer with azide compounds including hydrazine, and 2,6-bis(4-azidobenzylidene)-4-methylcyclohexanone (e.g. Ikeda, supra), or coupling to diamines as described by Kawaguchi, or Matsui, supra.

Also, when desired, a "monoamino" CD, wherein one amino group has been coupled, can be prepared through known methods, including limited or sterically determined monosulfonylation, and/or by specific protection and deprotection schemes. An amino-CD or amino-CD polymer, is suitably protected and/or deprotected as needed.

E. Diamino Derivatives

A previously sulfonylated CD or CD polymer is suitably iodinated so that it will couple to primary amino groups, using known methods (e.g. Ikeda or Iwakura, supra). Suitably, 10 gm of sulfonylated CD or CD polymer is combined with 12 gm of NaI on 200 ml of methanol, and mix at 70° C. for 48–60 Hrs. The iodinated CD product is collected by precipitation with acetone and purified by column chromatography.

The iodinated CD or CD polymer is coupled through an amino group to a suitable diamino substance. Suitable diamino substances are; 1,4-diaminobutane, 1,6-diaminohexane, 1,7-diaminoheptane, 1,8-diaminooctane, 1,10-diaminodecane, 1,12-diaminododecane, and other aliphatic, or aromatic, or heterocyclic carboxylic acids with two available amino groups for coupling. Coupling is done in a suitable solvent such as dimethylformamide (DMF), mixing 10 gm of iodinated CD polymer with a molar excess of the diamino substance (e.g. 10–20 gm of 1,6-diaminohexane), at 100° C. for 24 Hrs. The product, amino-CD (or amino-CD polymer), is concentrated and purified by column chromatography.

F. Protected Amino Groups

The amino groups introduced by various methods can be suitably protected by reaction with a halogenated alkylphthalimide such as N-(4-bromobutyl)phthalimide. After other suitable derivatizing, coupling and/or capping has been done, an amino group is deprotected by reaction with hydrazine in suitable solvent.

Also, the diamino substances of various chain lengths can be suitably derivatized before coupling. For instance, they can be "half protected" as trifluoroacetamidoalkanes at one of the amino ends, as described by Guilford, H., et al, Biochem. Soc. Trans. 3, 438 (1975), before coupling, and then suitably deprotected such as by hydrolysis or alcoholysis. Yet another suitable method involves the coupling of THP-protected amino-alkynes, previously described, to the iodinated CD or CD polymer and subsequent deprotection as needed.

G. Sulfhydryl-Cyclodextrin (SH-CD) Derivatives

A sulfhydryl group can be added to an amino-CD, suitably prepared as described previously, by coupling the appropriate thiolating agent to the available amino group. For instance, thiolation of available amino groups can be done by known methods using S-acetylmercaptosuccinic anhydride (SAMSA), (e.g. Klotz, Rector, or Lui, supra), SIAB, or 2-iminothiolane (e.g. Traut, supra). The sulfhydryl is protected as a disulfide during subsequent coupling reactions until it is exposed through disulfide cleavage.

Sulfhydryls can also be introduced through reaction of available hydroxyls with a suitable epoxy compound. For instance, epichlorohydrin or a suitable diepoxy crosslinker previously described, is coupled to a CD or CD polymer wherein free epoxy groups are produced. Free epoxy groups are then reacted with sodium thiosulfate to give thiosulfate esters (e.g. Carlsson, supra). The thiosulfate esters are subsequently reduced to sulfhydryls with dithiothreitol.

H. Preparation of Carboxylic Acid CD Derivatives

A preferred method for adding carboxylate groups is to couple glutaric or succinic anhydride to a hydroxyl group on the CD, or CD dimer, trimer or polymer. This produces a terminal carboxylate which can then be protected by esterification as needed. Also, carboxylates can be derivatized to an NHS ester using N-hydroxysuccinimide and carbodiimide such as dicyclohexyl carbodiimide.

Alternatively, a previously sulfonylated CD or CD polymer can be suitably iodinated as previously described for diamino groups. An iodinated CD polymer or a dial-CD polymer is coupled through the amino group to a suitable amino-carboxylic acid to provide the desired length of spacer. Suitable amino-carboxylic acids are; 4-aminobutyric acid, 6-aminohexanoic acid, 7-aminoheptanoic acid, 8-aminocaprylic acid, 12-aminododecanoic acid, and other aliphatic, or aromatic, or heterocyclic carboxylic acids with an available amino group for coupling.

Coupling of amino-carboxylic acid to iodinated CD or CD polymer is done in a suitable solvent such as dimethylformamide (DMF), mixing 10 gm of iodinated CD polymer with a molar excess of amino-carboxylic acid (e.g. 10 gm of 6-aminohexanoic acid), at 100° C. for 24 Hrs. The product, CD-carboxylic acid, is concentrated and purified by column chromatography.

Coupling of amino-carboxylic acid to dial-CD or dial-CD polymer is done by reductive alkylation. In a suitable buffer (e.g. 0.1 M borate, pH 7.5–8.5), 0.1–0.5 M triethanolamine), 10 gm of dial CD polymer is mixed with a molar excess of amino-carboxylic acid (e.g. 10 gm of 12-aminodecanoic acid), at RT for 1–2 Hrs. The Schiff's base coupling is stabilized by suitable reduction with $NABH_4$ (e.g. 0.1–1 mg/ml), for 1–12 Hrs. The product, CD-carboxylic acid, is concentrated and purified by column chromatography and dried for subsequent reactions as needed.

I. Capping Cyclodextrins

Capping is a type of derivatizing defined herein as coupling any suitable chemical "capping substance" to two or more sites on the CD molecule so that the substance spans the area between the coupled sites. Preferably, the capping substance spans across one of the end openings of the CD molecule and thereby stops the passage of a guest molecule through the capped CD molecule.

The CD's used herein can be suitably complexed with one or more guest molecules and/or derivatized and/or capped before, during or after their incorporation into the water soluble CD polymer carrier of the instant invention. In addition, the derivatizing and/or capping can be a done to produce CD's with the desired substances coupled to specific locations on the CD molecule. In the preparation of CD derivatives for use as hosts for drugs or other agents, modifications that increase affinity between the host CD and guest(s) are preferred. For instance, the host CD's of this invention are preferably derivatized (e.g. methylated or benzylated), and/or capped by various means to increase host-guest affinity.

J. Derivatizing and Capping Substances

Preferably, the capping substance is coupled at the primary or secondary "end" of the CD molecule, forming a bridge across either (or both) opening(s) that includes suitable hydrophobic groups in the capping substance. The capping substances can be coupled directly to available hydroxyls on the CD, or they can be coupled to suitable functional groups such as; diamino (or triamino), compounds to iodinated CD, or azido compounds to sulfonylated hydroxyls, and/or through "spacers" added to the CD.

Suitable capping substances are 6-methylamino-deoxy and 6-methylamino-6-deoxy derivatives transformed to the corresponding N-formyl compounds, imidazoles, m,m'-benzophenone-disulfonyl chloride, p,p'-stilbene-disulfonyl chloride, diphenylmethane-p,p'-disulfonyl chloride, terephthaloyl chloride, dianhydrides such as 3,3',4,4'-benzophenonetetracarboxylic dianhydride and 3,4,9,10-perylenetetracarboxylic anhydride, azido compounds such as 2,6-bis(4-azidobenzylidene)-4-methylcyclohexanone, and derivatives of aurintricarboxylic acid (e.g. thionyl chloride derivatives, triammonium salts "aluminons"), among others (e.g. Szejtli, Emert, Tabushi, or Cramer, supra).

PREPARATION I

Cyclodextrin Polymer Carrier with Completely Entrapped Anthracene

The purpose is to prepare a water soluble (or colloidal) cyclodextrin polymer carrier with completely entrapped anthracene. In this preparation, beta cyclodextrin was cross-linked while complexed with anthracene at a molar ratio of 4:1. The procedure was to combine 10 ml of water containing 0.0002 moles of cyclodextrin with 1 ml of chloroform containing 0.0005 moles of anthracene. After about 15 minutes of mixing at about 20,000 rpm with a stainless steel impeller and Dremel motor, most of the solvent had evaporated. While still mixing, 0.4 ml of epichlorohydrin and 0.2 ml of 2 N NaOH was added. After about 20 minutes, the reaction was stopped by adding 0.4 ml of ethanolamine. The resulting solution was allowed to settle and examined over UV illumination.

The turbid solution had a greenish-yellow, fluorescent top layer indicating unincorporated anthracene. However, the aqueous phase of the solution showed a distinct blue fluorescence, indicating that some anthracene was complexed in the cross-linked cyclodextrin polymer suspended in the aqueous phase.

The preparation in the aqueous phase was separated and concentrated by evaporation and then extracted 3 times with 4 ml of fresh chloroform by mixing, settling and drawing off the solvent phase. The preparation was resuspended in water and produced a turbid suspension that was still blue fluorescent. Since chloroform extraction did not remove the anthracene, it showed that the anthracene was completely entrapped within the cyclodextrin polymer.

PREPARATION II

Cyclodextrin Polymer Carrier with Completely Entrapped 2AA

The purpose is to prepare a water soluble (or colloidal) cyclodextrin polymer carrier with completely entrapped 2-aminoanthracene (2AA). The procedure was to combine 0.5 ml of 4.4% beta cyclodextrin in water, with 0.02 ml of solution containing 80% 1,4 butanediol diglycidyl ether (BDE), 10% of 0.1 M guest molecule, 2-aminoanthracene in dimethylformamide, and 2.4% 2 N NaOH while mixing vigorously and incubating at 60° C.

After about 1 hour, 0.2 ml of 0.01 M $K_2HPO_4$ (K2 buffer, pH 8.6), and 0.02 ml more of BDE was added and mixed to continue the crosslinking. After about one half hour more, the mixture was mixed with 0.1 ml of 1M lysine for about 2.5 hours more. The preparation was then centrifuged for 8 minutes at 2500 rpm and 0.55 ml of supernatant was fractionated on a column of Sephadex® G-25 (14×0.8 cm) equilibrated with K2 buffer.

The 0.5 ml fractions were then collected and examined for color to indicate the presence of the guest molecule 2AA. Fractions were also tested for carbohydrate to indicate cyclodextrin polymer. To a 50 µl aliquot of polymer fraction in water was added 1 drop of test reagent (3 gm potassium dichromate, 10 ml conc. $H_2SO_4$ and 290 ml water). The mixture was heated gently to oxidize the samples. The intensity of the dark residue was graded on a scale of 1–10.

The carbohydrate test showed that the polymerized cyclodextrin was in fractions 4 through 8, which was in the area of the void volume determined previously with a blue dextran control sample. Also, yellow color was seen in corresponding fractions 4 through 6, showing that guest molecule 2AA could not be separated from the polymer on the column. The carbohydrate (cyclodextrin) test and yellow color test results for the column fractions are shown in the table below (Exper. Nov. 14, 1989).

| CD Polymer Fraction | 1 | 2 | 3 | 4 | 5 | 6 | 7 | 8 | 9 |
|---|---|---|---|---|---|---|---|---|---|
| Relative Carbohydrate | 0 | 0 | 5 | 9 | 10 | 10 | 10 | 9 | 5 |
| Yellow Color | No | No | No | Yes | Yes | Yes | No | No | No |

PREPARATION III

Cyclodextrin Polymer Carrier with Tethered Guest

The purpose is to first prepare a water soluble (or colloidal) cyclodextrin polymer using 1,4 butanediol diglycidyl ether (BDE) to crosslink with the cyclodextrin hydroxyl groups. Additional BDE molecules are allowed to randomly couple at only one end before excess lysine is added. The lysine is covalently incorporated by covalently coupling to free ends of the BDE previously coupled to the cyclodextrin. The combination of BDE and lysine functions as a spacer group on the cyclodextrin polymer. The fluorophore 2-aminoanthracene is then covalently tethered as a captured guest to the cyclodextrin polymer through the amino group on the BDE-lysine spacer using glutaraldehyde.

A. Preparation of Cyclodextrin Polymer and Incorporated Lysine

The procedure was to combine 2 ml of 4.4% beta cyclodextrin in water, 0.1 ml of 2 N NaOH and 0.116 ml of 1,4 butanediol diglycidyl ether (BDE) while mixing and incubating at 50° C. The molar ratio of BDE to cyclodextrin was about 5:1. After about 4 hours, a 0.5 ml aliquot of the mixture was mixed with 0.2 ml of lysine (0.8 M in water, neutralized) for about 1.5 hours. The CD polymer was then fractionated on a column of Sephadex® G-25 (21×0.8 cm) equilibrated with distilled $H_2O$ and pre-calibrated with free cyclodextrin.

The 1 ml fractions were then collected and tested for carbohydrate to demonstrate cyclodextrin polymer. To a 50 µl aliquot of polymer fraction in water was added 1 drop of test reagent (3 gm potassium dichromate, 10 ml conc. $H_2SO_4$ and 290 ml water). The mixture was heated gently to oxidize the samples. The intensity of the dark residue was graded on a scale of 1–10. The polymerized cyclodextrin was in the fractions (3–4) containing a carbohydrate peak that eluted well ahead of the free cyclodextrin control (which peaked at fraction 9). The CD polymer fractions (3,4) were pooled.

B. Preparation of CD Polymer with Tethered Fluorophore (FL-CD)

The CD polymer with lysine was then coupled through the lysine groups to the guest molecule 2-aminoanthracene by a two step glutaraldehyde method based on Guesdon, J -L, et al, J of Histochem. Cytochem. 27, 1131–1139 (1979). The procedure was to combine 0.9 ml of the CD polymer with 0.1 ml of 25% glutaraldehyde (in water) and 0.02 ml 2 N NaOH (starting pH 12), and mix for about 25 minutes. The mixture was fractionated to remove excess glutaraldehyde on a column of Sephadex® G-25 (9×0.8 cm) equilibrated with distilled $H_2O$, collecting 0.3 ml fractions. The polymer fractions were pooled in a 1.4 ml volume. The 2-aminoanthracene was then coupled by mixing in a total of 0.06 ml of 5 mM 2-aminoanthracene in methanol:chloroform (4:1) and 0.01 ml 2 N NaOH (starting pH 12). This was reacted for 4 hours then blocked with 0.1 ml of ethanolamine. The Schiff base coupling was stabilized by adding 0.01 gm of $NaBH_4$ and incubating overnight.

The mixture was then neutralized with 1 N HCl and excess 2-aminoanthracene was removed by fractionating on a column of Sephadex® G-25 (9×0.8 cm) equilibrated with distilled $H_2O$, collecting 0.5 ml fractions. The fractions were then tested for carbohydrate as described previously and those with carbohydrate were also tested for guest molecule using chemiluminescence (CL). The CL procedure was to activate the 2-aminoanthracene using oxidation of bis(2,4, 6-trichlorophenyl) oxalate ester (TCPO). Into an FL-CD sample (0.02 ml in 0.1 ml of 0.1 M $K_2HPO_4$), was added 0.01 ml 0.22% TCPO in ethyl acetate. After placing the sample into a dark chamber in the luminometer, 1 ml of 0.4 M $H_2O_2$ was injected and the light emission recorded on a chart recorder. The carbohydrate (cyclodextrin) test and CL test results for the fractions are shown in the table below (Exper. CD/1).

| FL-CD Polymer Fraction | 1 | 2 | 3 | 4 | 5 | 6 | 7 | 8 | 9 |
|---|---|---|---|---|---|---|---|---|---|
| Relative Cyclodextrin | 5 | 7 | 9 | 9 | 10 | 8 | 6 | 5 | NT |
| Relative CL Emission | .25 | .30 | 3.33 | 10.0 | >10 | 3.6 | 1.1 | .40 | .28 |

These data show that the carbohydrate peak also corresponds to the most fluorophore CL activity. This CL activity shows that the guest molecule 2-aminoanthracene is coupled to the CD polymer and could not be separated by column chromatography.

PREPARATION IV

Cyclodextrin Polymer Carrier Targeted with Antibody Protein

The purpose is to synthesize a targeted cyclodextrin polymer carrier by covalently coupling a biorecognition molecule to a cyclodextrin polymer carrier. In this example, the carrier was prepared as in Preparation III, and the biorecognition molecule is antibody protein.

A. Preparation of FL-CD Polymer with Coupled N-hydroxysuccinimidyl (NHS) Ester

In this step a cyclodextrin polymer carrier is covalently coupled with NHS ester to form a NHS-CD. FL-CD polymer carrier (with tethered 2-aminoanthracene) was prepared as above and fractionated by column chromatography using Sephacryl® S200 in a 1.5×18.5 cm column equilibrated with water (Exper. CD/8). The purified FL-CD was collected in 1 ml fractions #8–19, and pooled to give a greenish-yellow fluorescent solution. The solution was dried at 60° C. to give about 0.36 gm. The product was dissolved in water and titrated to pH 6 with 6 N HCl giving 0.144 gm FL-CD polymer carrier per ml.

The procedure is to form NHS esters with the carboxylic acid groups on the lysine that is incorporated into the FL-CD polymer carrier. To 1 ml of dissolved FL-CD polymer carrier was added 0.1 gm of N,N'-dicyclohexylcarbodiimide (DCC) and mixed to dissolve. Then 0.1 gm of N-hydroxysuccinimide was added with mixing. After about 1.5 hours, 0.05 ml of glacial acetic acid was added and mixed about 25 minutes. To the mixture was added about 4 ml of anhydrous methanol, then it was mixed, centrifuged and the light yellow supernatant was collected. The resulting solution of FL-CD polymer with coupled NHS ester groups was concentrated by evaporation and stored in the refrigerator.

B. Coupling of Gamma Globulin with the FL-CD Polymer Carrier

In this step the purpose is to covalently couple antibody protein (human gamma globulin) to cyclodextrin polymer carrier with tethered guest 2-aminoanthracene. To a glass test tube was added 0.2 ml of 0.1 M $K_2HPO_4$, pH 8.5 in water, 0.1 ml 1.6% human gamma globulin and 0.2 ml of 50% methanol containing about 0.09 gm/ml of FL-CD polymer carrier with coupled NHS ester. The pH of the mixture was adjusted to about pH 7 with 2 N NaOH and incubated about 2 days at RT. The labeled protein was recovered by precipitation by adding 1.5 ml of 52% $(NH_4)_2SO_4$ in water to the mixture and centrifuging to collect the precipitate. The precipitate was dialyzed against distilled water to remove $(NH_4)_2SO_4$ and concentrated to a final volume of 0.11 ml.

Aliquots of the targeted cyclodextrin polymer carrier were tested for CL activity using TCPO as described previously. The peak height of CL activity of the carrier was low but the CL activity continued for a longer time when compared to the FL-CD polymer carrier alone and to control gamma globulin. The CL activity showed that the gamma globulin biorecognition molecule was coupled to the FL-CD polymer carrier.

PREPARATION V

Cyclodextrin Polymer Carrier with Completely Entrapped Paclitaxel (Taxol)

The purpose is to synthesize a water soluble (or colloidal) cyclodextrin polymer carrier that contains completely entrapped paclitaxel (PTX) and the polymer includes acid-labile hydrazone linkages that provide controlled release.

The following is a schematic of the cyclodextrin reactions employed.

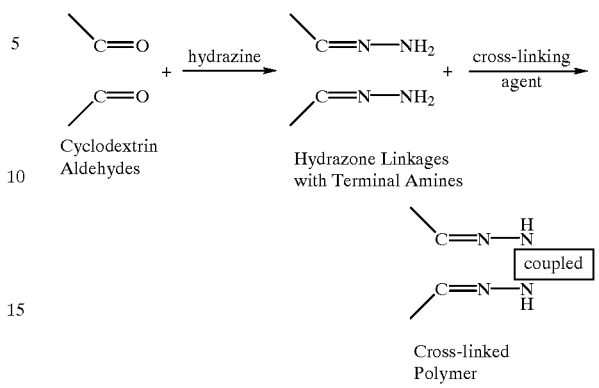

A. Preparation of Dialdehyde CD Using Oxidation

The purpose is to oxidize the cyclodextrin (CD) to produce dialdehydes that can subsequently be reacted with hydrazine to form an acid-labile hydrazone linkage. The hydrazone linkages on each cyclodextrin will also have terminal amino groups for subsequent crosslinking to make the polymer carrier.

The oxidation procedure is based on published methods used to oxidize other polysaccharides and specifically cyclodextrins (Kobayashi, supra) This method introduces dialdehyde groups at the C-2, C-3-trans-diol position of the cyclodextrin glucose residues.

The procedure was to add sodium m-periodate ($NaIO_4$) to 30 mM cyclodextrin in 100 ml of water while mixing at 30° C. in the dark. The molar ratio of $NaIO_4$ to cyclodextrin was 2:1, to give 1 to 2 dialdehydes per CD molecule. The reaction was continued in the dark for 6 to 8 hours. Remaining $NaIO_4$ was consumed with a molar excess of ethylene glycol. The resulting dialdehyde cyclodextrin (dial-CD) was fractionated using gel filtration on a Sephadex™ G-25column. The more open dial-CD molecules have been found to elute ahead of the native CD. The fractions was concentrated by evaporation under vacuum.

The amount of CD (mw 1135) as carbohydrate in each fraction is monitored by a colorimetric test for carbohydrates. To 2 ml of water containing diluted dial-CD fraction (0.01–0.05 mg) is added 0.05 ml of 80% phenol. Then 5 ml of concentrated sulfuric acid is added rapidly to mix. Color is allowed to develop 20 minutes at 25–30° C. and the absorbance is read at 490 nm. The absorbance is compared to a series of identically treated CD standards at 0.005, 0.01, 0.02, 0.04, 0.08 and 0.1 mg per ml $H_2O$.

B. Preparation of Hydrazone Linkages on the CD

This reaction involves a condensation reaction of the hydrazine with available aldehydes to produce a hydrazone linkage. The objective is to react dial-CD with enough hydrazine so that ideally each available aldehyde is coupled to a single hydrazine with minimal cross-linking. The dial-CD preparation is dissolved in water to give starting concentrations of 30 mM. While stirring the solution at room temperature, a 3 to 4-fold molar excess of hydrazine (Sigma) is added with continued stirring for 2 hours. The resulting hydrazone cyclodextrin (Hz-CD) is fractionated on a Sephadex™ G-15 column and the fractions dried to constant weight by vacuum evaporation.

The number of amino groups is determined colorimetrically using a Blue G-250 assay reagent for protein (Reagent Kit Cat #23200, Pierce, Rockford, Ill.) with the absorbance read at 595 nm. To ensure that enough amino groups are available, the Hz-CD fractions with at least 2 free amino groups available per mole are used in the next step.

C. Preparation of CD Polymer with Completely Entrapped Drug

The purpose is to cross-link Hz-CD to form a water soluble (or colloidal) cyclodextrin polymer carrier that is acid-labile. The polymers preferably have molecular weights of 20,000–50,000. In this procedure the Hz-CD monomers are cross-linked through the terminal amino groups on the hydrazine derivatives.

In order to entrap the drug, the paclitaxel (PTX) is dissolved in a solvent and mixed with the Hz-CD to form inclusion complexes. Then the Hz-CD is cross-linked to form the polymer and completely entrap the drug in polymer aggregates.

Preparations can be made with molecular ratios between 1:1 and 1:8 of PTX to Hz-CD. A near saturated suspension of Hz-CD is prepared in 0.05 M phosphate buffer, pH 7.5 (PB). The PTX in dichloromethane (2 mM) is added with vigorous mixing (20,000 rpm impeller). While mixing, the drug is exposed to the aqueous phase to allow complexes to form between the PTX and Hz-CD. Mixing is continued for 15 minutes to one hour. The cross-linking reagent is then be added while continuing to mix.

At this point, a variety of amino-reactive, bifunctional cleavable or noncleavable agents with different spacer lengths can be used to cross-link amino groups. For this example, cross-linking is done with a bifunctional, cleavable coupling agent (Tech. Bull. #0544, Pierce Chem. Co., Rockford, Ill.), dithiobis(succinimidyl propionate) (DSP, spacer length 12 angstroms). During polymerization, the objective is to completely entrap the drug in polymer aggregates that are soluble (or colloidal). The cross-linking reaction is run for about 3 hours or just before insoluble polymers form.

The resulting PTX-loaded CD polymer (PTX-CD) is then fractionated by gel exclusion chromatography on pre-calibrated columns of Sephacryl® S200-HR (40×5 cm) equilibrated with PB. Pre-calibration is done using various molecular weight dextrans (i.e. 15,000 to 60,000, Sigma) in separate runs.

The PTX-CD fractions that elute in molecular weight ranges between 20,000 and 50,000 are vacuum dried at 50° C. and weighed. For some procedures, fractions may be concentrated by centrifugal filtration using suitable molecular weight cutoff filter tubes (Micron Separations Inc., Westboro, Mass.). Other fractions of higher or lower molecular weight may also be suitable. The approximate moles of product is calculated as total grams of dried carrier divided by the apparent molecular weight.

Alternatively, suitable derivatives of cyclodextrin can be used to prepare the carrier. Preferred CD derivatives are hydroxypropyl cyclodextrin (HPCD) and 2,3-dihydroxypropyl cyclodextrin (DHPCD). For oxidation to dialdehyde, a preferred form of HPCD or DHPCD is one with 3–4 degrees of substitution with propylene oxide or glycidol (Pitha, supra).

Alternatively, other cross-linkers that provide longer spacer lengths to avoid steric hindrance can be used. One example is ethylene glycol bis(succinimidylsuccinate) (EGS, 16.1 angstrom spacer). EGS is cleavable with hydroxylamine Also, the Hz-CD can be polymerized using the water soluble bifunctional reagent dimethyl adipimate (DMA, 8.6 angstrom spacer, Technical Bull. #0438, Pierce). The parameters of molar ratios and reaction times for cross-linking Hz-CD with DMA are suitably optimized for the desired polymer size. A near saturated suspension of Hz-CD and PTX in chloroform is prepared in PB with vigorous mixing as described previously. As the solvent evaporates, the drug is forced into the aqueous phase to allow complexes to form between the PTX and Hz-CD. The DMA is added and mixed for 2–6 hours. The resulting PTX-CD is fractionated by gel exclusion chromatography as described previously. The hydrazone linkages provide controlled release when hydrolyzed to release free drug maximally at pH 4–5.

PREPARATION VI

Targeted Cyclodextrin Polymer Carrier with Completely Entrapped Doxorubicin

A. Preparation of CD Polymer with Incorporated Amino Groups

The purpose is to cross-link gamma cyclodextrin (Mol. Wt. 1297), to form a water soluble (or colloidal) cyclodextrin polymer carrier that has completely entrapped doxorubicin (DOX). Cyclodextrins are crosslinked through their hydroxyl groups to each other using 1,4 butanediol diglycidyl ether (BDE, Mol.Wt. 202.2).

In order to entrap the drug, the DOX is dissolved in a solvent and mixed with the CD to form inclusion complexes. Then the CD is cross-linked to form the polymer and completely entrap the drug in polymer aggregates.

A preparation is made to give a molecular ratio between 1:2 and 1:8 of DOX to CD. While mixing, the drug is exposed to the CD to allow complexes to form between the DOX and CD. The procedure is to combine near saturated DOX with 100 ml of 4.0% cyclodextrin in 20% (v/v) dimethylformamide (DMF) in water, with 5 ml of 2 N NaOH (starting pH 13), with vigorous mixing (20,000 rpm impeller). The cross-linking reaction is initiated by adding 10 ml of 95% BDE while mixing and incubating at 60° C.

The reaction is conducted for 2–6 hours followed by the addition of a molar excess of lysine (0.75 ml of 4 M lysine in water, adjusted to pH 8). Lysine is incorporated into the polymer as the BDE cross-links the lysine through one of its amino groups to the cyclodextrin. The excess lysine also couples to and blocks any remaining free BDE. Mixing is continued for one more hour and the mixture is then neutralized with 1 N HCl.

Aliquots of the drug-loaded CD polymer carrier are then fractionated by gel exclusion chromatography on pre-calibrated columns of Sephacryl® S200-HR (40×5 cm) equilibrated with distilled $H_2O$. Pre-calibration is done using various molecular weight dextrans (i.e. 15,000 to 60,000, Sigma) in separate runs.

The carrier fractions that elute in molecular weight ranges between 20,000 and 50,000 are taken to the next step. Other fractions of higher or lower molecular weight may also be suitable. The fractions are then vacuum dried at 50° C. and weighed. The approximate moles of product is calculated as total grams of dried carrier divided by the apparent molecular weight. The relative amount of CD in the fractions can be monitored by a colorimetric test as described previously. The CD polymer fractions can also be tested for the presence of amino groups as described previously.

If needed, additional lysine molecules can be added to the PolyCD. The procedure is to again treat the carrier with BDE as described above, but for only 20–30 minutes. Additional amino groups are then introduced with the excess lysine treatment and the product is fractionated on Sephacryl® as described.

Alternatively, a selective derivatization procedure can be used that takes advantage of the more reactive primary hydroxyls. The procedure is to first "tosylate" two or more primary hydroxyls on each cyclodextrin and then replace the tosyl groups with amino groups. The cyclodextrins are then complexed with the DOX and polymerized by cross-linking through the aminos using a bifunctional cross-linking agent.

The tosylation step is done by reacting 12 grams of cyclodextrin with 9 grams of p-toluenesulfonyl chloride (tosyl chloride) in 100 ml of anhydrous pyridine solvent. The tosyl chloride is added in 3 gram aliquots over a 36 hour period with constant stirring of the mixture for a total of 48 hours. The reaction is stopped with 20 ml of methanol. The product is precipitated, filtered and washed with 200 ml aliquots of chloroform, then dried.

The tosyl groups are substituted for azide by dissolving 1.3 gm of the tosylated cyclodextrin in 100 ml of dimethylformamide (DMF) and adding 1 gm of sodium azide. The mixture is heated with stirring to 100° C. for 2 hours and the product is collected from dried supernatant. The product is dissolved in 10 ml of water, precipitated with acetone and dried.

The azide cyclodextrin is reduced to the amine by dissolving 1 gm in 100 ml of 20% methanol/water containing 0.4 gm of palladium black catalyst (Sigma). The mixture is stirred 1 hour under H2, then filter through Celite. The amino-derivatized cyclodextrin is collected by drying.

The resulting amino-cyclodextrin (amino-CD), can then be complexed with DOX and polymerized using the water soluble bifunctional reagent dimethyl suberimidate (DMS, Mol. Wt 273.2), which is routinely used to selectively couple amino groups (Technical Bull., Pierce).

The parameters of molar ratios and reaction times for cross-linking amino-CD with DMS are optimized for the desired polymer carrier. Typically, to 100 ml of 4.0% amino-CD previously complexed with DOX in 0.2 M triethanolamine HCl, pH 8.5 in water, is added 4 gm of DMS and mix at 60° C. for 2–6 hours. The reaction is stopped by the addition of a molar excess of lysine (4 M, adjusted to pH 8). Lysine is incorporated into the polymer as the DMS cross-links the lysine and additional amino groups are available for coupling to antibody. The excess lysine also couples to and blocks any remaining free DMS. The mixing is continued for one more hour and the mixture is then neutralized with 1 N HCl. The resulting polymer is fractionated by gel exclusion chromatography as described previously. Alternatively, other anticancer drugs can be used such as daunomycin, puromycin or ellipticine.

B. Introduction of Sulfhydryl Groups by Thiolating Amines on the CD Carrier

The CD polymer carrier is thiolated by modifying the lysine residues using 2-iminothiolane (FW 137.6), based on the technical bulletin from Pierce Chem. Co. The number of available amino groups on the carrier can be determined as described previously. The molar ratio that is used between the carrier and 2-iminothiolane is about 1:10.

The reaction is carried out by combining 0.4 mmoles of carrier dissolved in 0.16 M borate buffer (pH 8.0), and 4 mmoles of 2-iminothiolane. The mixture is mixed for about 2 hours at room temperature. The resulting thiolated carrier is separated by gel chromatography using a Sephadex® G15 column equilibrated with 0.05 M phosphate buffer, pH 7.5.

Aliquots of the thiolated carrier can be tested for the presence of sulfhydryl groups. The test for sulfhydryl is a standard test that employs 5,5'-dithiobis(2-nitrobenzoic acid, DTNB). The procedure is to combine 0.1 ml of thio-polyCD samples diluted in water with 1 ml of deoxygenated 0.2 M Tris buffer, pH 8.2, and add 0.1 ml of 0.01 M DTNB in deoxygenated methanol. Color is allowed to develop for 30 minutes and the absorbance is read at 412 nm on a spectrophotometer. The results are compared to a standard curve of identically tested dilutions of 2-mercaptoethanol. The goal is to introduce an average of at least three sulfhydryl groups (2-mercaptoethanol molar equivalents), for each mole of thiolated carrier.

C. Conjugation of the Thiolated CD Carrier to the Maleimide-Activated Antibody

The molar ratio of thiolated carrier to antibody is 4:1. For instance, 0.02 mmoles of the 20,000 molecular weight fraction of thiolated carrier is conjugated with 0.005 mmoles of the MBS-antibody (MW 140,000). Other molar ratios of thiolated carrier to antibody can be used during conjugation.

The conjugation reaction is to combine freshly prepared MBS-antibody with thiolated carrier in 0.05 M phosphate buffer, pH 7.5, and stir for 2 hours at room temperature. The conjugate is fractionated by gel exclusion chromatography using bovine IgG calibrated Sephacryl® S200-HR column equilibrated with the same buffer. The fractionated conjugate is collected in a fraction collector equipped with an ultraviolet monitor set at 280 nm to detect the IgG. The conjugate is in the fractions containing IgG and corresponding to molecular weights greater than 200,000.

The conjugate fractions can be tested for protein content using the Bradford colorimetric method and tested for carbohydrate as described previously. Fractions greater than 200,000 molecular weight are pooled and concentrated by centrifugation filtration using 100,000 molecular weight cutoff filter tubes (Micron Separations Inc., Westboro, Mass.) or by precipitation with ammonium sulfate and dialysis against PB.

PREPARATION VII

Coupling Methods for Targeting Cyclodextrin Polymer Carriers

These are methods for synthesizing cyclodextrin polymer carriers wherein a coupling group is included in the composition to provide for coupling to any suitable biorecognition molecule with a suitable functional group. The biorecognition molecule can be a suitable protein, including antibodies and avidins or streptavidin, or ligands, or nucleic acids.

A. Preparation of NHS-CD Polymer Carriers

In a suitable anhydrous solvent such as DMF, the CD-carboxylic acid polymer is combined with N-hydroxysuccinimide and an aromatic carbodiimide such as N,N-dicyclohexylcarbodiimide, at approximately equimolar ratios and reacted at RT for 1–3 Hrs. The product, N-hydroxysuccinimide cyclodextrin (NHS-CD), is separated in the filtrate from precipitated dicyclohexylurea, collected by evaporation and purified by chromatography.

Under appropriate conditions, NHS-CD polymer derivatives can be prepared by coupling NHS esters directly to amino-CD or amino-CD polymer. Preferably, the NHS ester is a bifunctional NHS coupling agent with a suitable spacer. Suitable NHS coupling agents for use in this invention have been previously described, including DSS, bis (sulfosuccinimidyl)suberate ($BS^3$), DSP, DTSSP, SPDP, BSOCOES, DSAH, DST, and EGS, among others.

B. Preparation of Sulfhydryl-CD Polymer Carriers

Sulfhydryls on polymer carriers can be used for disulfide coupling to other available sulfhydryls on the desired biorecognition molecule such as antibodies, or avidins, or streptavidin, or ligands, or nucleic acids. If needed, the available sulfhydryls can be introduced by thiolation of the biorecognition molecule before coupling. Alternatively, a sulfhydryl-containing CD polymer carrier is coupled to any maleimide derivative of protein, ligand, nucleic acid or biotin, (e.g. biotin-maleimide) or iodoacetyl derivatives such as N-iodoacetyl-N'-biotinylhexylenediamine.

C. Maleimido-Cyclodextrin Polymer Carriers and Iodo-Cyclodextrin Polymer Carriers The maleimido-cyclodextrin polymer carriers (Mal-CD), of this invention are suitable for coupling to native or introduced sulfhydryls on the desired biorecognition molecule.

A maleimido group is added to an amino-CD polymer carrier suitably prepared as described previously, by coupling a suitable hetero-bifunctional coupling agent to the available amino group. The hetero-bifunctional coupling agent consists of a suitable spacer with a maleimide group at one end and an NHS ester at the other end. Examples are previously described and include MBS, SMCC, SMPB, SPDP, among others. The reaction is carried out so that the NHS ester couples to the available amino group on the CD polymer carrier, leaving the maleimide group free for subsequent coupling to an available sulfhydryl on a biorecognition molecule.

Under appropriate conditions, Iodo-Cyclodextrin (Iodo-CD) polymer carriers can be prepared for coupling to sulfhydryl groups. For instance, NHS esters of iodoacids can be coupled to the amino-CD polymers. Suitable iodoacids for use in this invention are iodopropionic acid, iodobutyric acid, iodohexanoic acid, iodohippuric acid, 3-iodotyrosine, among others. Before coupling to the amino-CD polymer, the appropriate Iodo-NHS ester is prepared by known methods (e.g. Rector, supra). For instance, equimolar amounts of iodopropionic acid and N-hydroxysuccinimide are mixed, with suitable carbodiimide, in anhydrous dioxane at RT for 1–2 Hrs, the precipitate removed by filtration, and the NHS iodopropionic acid ester is collected in the filtrate. The NHS iodopropionic acid ester is then coupled to the amino-CD polymer carrier.

PREPARATION VIII

Biotinylated Cyclodextrin Polymer Carriers

Biotinylated CD polymer carriers can be produced by a variety of known biotinylation methods suitably modified for use with CD's. For instance, combining an amino-CD polymer derivative with a known N-hydroxysuccinimide derivative of biotin in appropriate buffer such as 0.1 M phosphate, pH 8.0, reacting for up to 1 hour at room temperature. Examples of biotin derivatives that can be used are, biotin-N-hydroxysuccinimide, biotinamidocaproate N-hydroxysuccinimide ester or sulfosuccinimidyl 2-(biotinamino)ethyl-1,3'-dithiopropionate, among others.

Through the use of suitable protection and deprotection schemes, as needed, any CD polymer carrier of the instant invention can be coupled to biotin or a suitable derivative thereof, through any suitable coupling group. For instance, biocytin can be coupled through an available amino group to any NHS-CD label described herein. Likewise, thiolated biotin can be coupled to any mal-CD polymer carrier.

The biotinylated CD polymer carrier can be used to couple a plurality of carriers an intermediate. For instance, by combining dilute solutions of the biotinylated CD carrier with avidin or streptavidin in the appropriate molar ratio, 1, 2 or 3 biotinylated CD carriers will couple to the avidin or streptavidin and produce a complex with one or more biotin-binding sites still available.

PREPARATION IX

A Cyclodextrin Polymer Carrier Prepared on a Solid Support

Another embodiment for a water soluble (or colloidal) cyclodextrin polymer carrier can be synthesized with a more predictable number of CD molecules, giving new advantages of uniform structure and chemical properties. The synthesis method is to couple an initial CD molecule (or derivative) to a solid support using a cleavable coupling agent. Then additional CD molecules (or CD derivatives with or without protected groups) are attached to the first CD in a controlled, step-wise manner. Alternatively, a suitable intermediate substance (i.e. amino derivatized HPMA) can be initially coupled to the solid support and CD molecules coupled to it. After the desired number of CD molecules have been linked together to form an open polymer, the desired drug or other active agent is allowed to complex with the polymer. Then the polymer is further cross-linked to close the polymer and completely entrap the active agent. The loaded carrier is then cleaved from the solid support.

The CD molecules used in this procedure can include tethered guests and antenna substances, and be suitably derivatized and/or capped before coupling to incorporate other desirable features. However, it is preferred that each CD molecule (or dimer, or trimer), that is coupled, has a well defined structure to facilitate the production of CD polymer carriers with uniform and consistent properties.

A variety of suitable materials, such as those used in chromatography (e.g. Smokova-Keulemansova, supra), can be used for a solid support. The solid support can be in the form of particles, beads, fibers, plates, and tubing walls, and composed of styrenes, acrylamides, silica gels, solid or porous glass, dextrans, and celluloses, among others that are suitably derivatized as needed and compatible with the reactions used.

The initial coupling agent used to couple the initial CD or intermediate substance to the support is preferably one that is readily cleaved when desired. Suitably, the initial coupling agent is a bifunctional, amino-reactive reagent such as those with a cleavable disulfide group, including DTBP, DSP, DTSSP and photoactive couplers like BASED, SADP, SAND, and SASD. Other suitable initial amino-reactive coupling agents are periodate cleavable, such as DST and sulfo-DST, or hydroxylamine cleavable at the ethyl ester linkage, such as EGS and sulfo-EGS.

The coupling agents used to couple subsequent CD's to make an open polymer are preferably noncleavable, or biocleavable, or cleavable by a different mechanism than the initial coupling agent. When coupling through amino-derivatized CD molecules, amino-reactive, bifunctional coupling agents such as DMA, DMP, DMS, DSS and DSG would be used. When coupling through sulfhydryl-derivatized CD molecules, sulfhydryl-reactive, bifunctional coupling agents would be used such as MBS. Diepoxy coupling agents such as BDE can be used to couple through amino, sulfhydryl or hydroxyl functional groups.

In another embodiment, when the carrier is cleaved from the support after synthesis, it can leave a suitable functional group for targeting by subsequently coupling a biorecognition molecule to the carrier. Or, the remaining functional group can be converted to an NHS ester by various known means for subsequent coupling to an amino group on a biorecognition molecule.

CD Polymer Carrier Synthesis

A suitable method for synthesizing water soluble (or colloidal) cyclodextrin polymer carriers of the instant invention is as follows;

1. A suitable amino-derivatized solid support is prepared. For instance, porous glass beads or predried silica gel is amino-derivatized with (3-aminopropyl)trimethoxysilane. The solid support is then treated for coupling (activated), with a bifunctional, cleavable disulfide coupling agent, DSP. The uncoupled reagents are removed.

2. To the support is added for coupling, an excess of amino-CD derivative, 2,3 dihydroxypropyl beta cyclodextrin (amino-DHPCD) or amino-derivatized (amino-HPMA). The uncoupled reagents are removed.

3. The initial CD or intermediate substance is then treated for additional coupling (activated) with a suitable bifunctional coupling agent that will react with the initial CD and subsequently couple to additional CD molecules. For instance, with amino-DHPCD or amino-HPMA, an amino-reactive agent such as DSS is used. Or, the initial CD or intermediate substance can be treated with a diepoxy such as BDE. The unreacted coupling agent is then removed.

4. An excess of amino-DHPCD molecules (which may include some halogenated alkylphalimide protected amino groups) are then added to covalently couple to the initial CD or intermediate substance. The unreacted amino-DHPCD molecules are then removed.

5. The immobilized preparation is then treated again for additional coupling with a suitable bifunctional coupling agent such as DSS or BDE. The unreacted coupling agent is then removed.

6. Another cycle of excess amino-DHPCD molecules are then added as before to covalently couple to the preparation and unreacted reagent is removed.

7. Depending on how large an open polymer is desired, the steps are repeated of activating the preparation again with coupling agent, removing the unreacted agent, adding excess amino-DHPCD molecules for coupling and removing the unreacted CD molecules. After the last cycle of DHPCD molecules have been coupled to the preparation, unreacted molecules are removed.

8. To the open polymer preparation the desired drug or other active agent is added and allowed to complex with the polymer. In this example, puromycin is added to allow inclusion complexes to form with the polymer.

9. Then the drug-loaded polymer is further cross-linked to close the polymer and completely entrap the active agent. In this example, the amino-reactive coupling agent DSS is used to cross-link the available amino groups. If employed, previously protected amino groups are made available by a deprotection step before final cross-linking.

10. The drug-loaded cyclodextrin polymer carrier is then cleaved from the solid support by reduction of the disulfide bond in the initial coupling agent.

Other modifications can be included before final cleavage. For instance, acid-labile linkages can be incorporated into the final cross-linking to provide controlled release of entrapped active agent. In one embodiment, vicinal hydroxyls on the DHPCD molecules of the open polymer can be oxidized to dialdehydes using Na metaperiodate. The dialdehydes are then coupled to hydrazine to provide acid-labile hydrazone linkages with terminal amino groups.

The open polymer is then loaded with drug as before and then closed by cross-linking the terminal amino groups. The final cross-linking is done using a bifunctional, amino-reactive coupling agent such as DSS or BDE. Also, the drug-loaded carrier can be treated with acetic or succinic anhydride to give carboxylates that are converted to NHS esters through reaction with carbodiimides and N-hydroxysuccinimide. The carrier is then targeted by coupling it to a suitable biorecognition molecule.

PREPARATION X

A Cyclodextrin Polymer Carrier Prepared From a Cyclodextrin Monolayer

Another embodiment for a water soluble (or colloidal) cyclodextrin polymer carrier can be synthesized wherein the cyclodextrin monomers are first cross-linked to form an open polymer that is in the form of a sheet or layer of cross-linked cyclodextrin molecules. This embodiment can provide new advantages of organized structure and chemical properties.

In the first step of the synthesis method, CD molecules (or CD derivatives such as HPCD or DHPCD) are positioned on a surface so that their primary or secondary ends are facing the surface and their edges are within coupling distance of each other. Ideally, all of the CD molecules are oriented in the same direction. One way of accomplishing this is to prepare a surface (i.e. a solid support or flexible surface) onto which guest molecules have been covalently coupled (i.e. through spacer groups) so that each guest is available to form an inclusion complex with a cyclodextrin. Suitably, guest molecules are used that force the cyclodextrin molecules to bind to them in only one orientation. For instance, if the guest molecules are just big enough, they will form the strongest binding inclusion complex by only entering the larger, secondary end of the cyclodextrin molecule and not the smaller primary end. Examples of the most preferable inclusion compounds, especially with aromatic compounds, are well known for alpha CD, beta CD and gamma CD. For instance, anthracene derivatives bind primarily through the secondary end of beta CD and pyrene derivatives bind primarily through the secondary end of gamma CD.

In this example, 2-aminoanthracene is coupled to amino-derivatized glass beads using a bifunctional NHS coupling agent such as DSS. The 2-aminoanthracene is immobilized in very high density so that many molecules are within one beta CD diameter's distance apart (i.e. about 6 angstroms). Then in suitable solvent or aqueous buffer, beta CD is mixed with the beads to form inclusion complexes with the immobilized 2-aminoanthracene on the bead surface. The excess CD may be removed.

Then the complexed CD molecules are cross-linked with a diepoxy such as BDE, or a triepoxy such as glycerol propoxylate triglycidylether, so that every CD molecule is coupled to at least two (preferably 3 or 4) of its neighbor CD molecules. Alternatively, derivatized CD molecules can be used such as amino-CD or amino-HPCD or amino-DHPCD, and then cross-linked using a cleavable, bifunctional coupling agent such as DSP, DST or EGS. Also, amino-CD molecules can be cross-linked using a suitable biocleavable coupling agent described herein.

The resulting open polymer is a sheet or monolayer of CD molecules (or CD derivatives with or without protected groups). The resulting CD monolayer is then removed from the immobilized 2-aminoanthracene molecules by using a suitable competing solvent or surfactant to cause dissociation.

The CD monolayer is then mixed, in suitable solvent or aqueous buffer, with a drug or other active agent (i.e. paclitaxel) to allow the monolayer to form inclusion complexes with the drug. The drug-loaded CD monolayer is then further cross-linked to close the polymer and completely entrap the drug. The resulting CD monolayer carrier can also be targeted by coupling it to a biorecognition molecule. The CD monolayer carrier can be further derivatized to provide functional groups that are then used for coupling to the biorecognition molecule.

PREPARATION XI

CD Polymer Carriers with Antenna Substances

A new water soluble (or colloidal) CD polymer carrier with potentially greater cytotoxic or catalytic efficiency can be synthesized by incorporating antenna substances. An antenna substance is defined as certain light and/or energy collecting substances that transfer the energy to a catalyst or energy emitter in the carrier. The various antenna substances of the invention can be conjugated and/or noncovalently coupled in "close proximity" so that they will cooperatively participate in an energy transfer reaction resulting in the emission of energy or a product. The most preferred application is in photodynamic therapy where photoactive agents are used to kill cancer cells.

The antenna substances can be coupled to the carrier in various ways to promote the most efficient cytotoxic or catalytic activity. For instance, the antennas can be covalently coupled to the CD derivative or CD polymer, to the guest photoactive agent, or to an intermediate substance that is part of the CD carrier. Certain photosynthetic antenna substances (e.g. chlorophylls, pigments) can also be coupled noncovalently to the CD carrier through binding to certain polypeptides (e.g. from photosynthetic plants, algae and bacteria), which are then covalently bound to the CD carrier. Examples of photosynthetic substances are described by H. Zuber, TIBS 11, 414–419, October, 1986, and J. Deisenhofer, et al, Science 245, 1463–1473 (1989), the contents of which are incorporated herein by reference.

Suitable antenna substances are any aliphatic, aromatic or heterocyclic compounds that are capable of collecting light energy or photons. The most preferred antenna substances for use in photodynamic therapy are those that absorb infrared and far infrared light. Examples include carotenoids, folic acids, retinols, retinals, rhodopsins, viologens, chlorophylls, bacteriochlorophylls, phycobiliproteins, phycoerythrins, porphyrins, $MCe_6$, open chain tetrapyrroles (bilins), tryptophan and/or tyrosine-containing substances (e.g. polypeptides), Rose Bengal, fluorophores, scintillators, and various derivatives, analogs and precursors of the antenna substances.

PREPARATION XII

Cyclodextrin Catalyst Agent

A cyclodextrin catalyst agent is a new invention defined herein as a cyclodextrin derivative of an individual cyclodextrin, or dimer, trimer or polymer, wherein the CD derivative host functions as an "artificial enzyme", and certain guest molecules function as chemical substrates. When the chemical substrate comes in contact with the cyclodextrin catalyst agent under appropriate conditions, it is modified to produce a product that is inhibitory or toxic to certain cells, microbes or parasites. In one embodiment, the CD catalyst agent is coupled to a biorecognition molecule for targeting specific infected cells, cancer cells, tissues or disease organisms.

With suitable derivatization, the CD catalyst agents can be synthesized to bind and modify prodrugs into active drugs and modify other specific substrates. The CD catalyst agent can also catalyze specific reactions such as generate free radicals, including singlet or triplet oxygen that directly kills infected cells, cancer cells, or disease organisms. Suitably, the CD catalyst agent requires derivatives that provide a "recognition site" and one or more "catalytic groups" on the CD agent (e.g. references; Ikeda, VanEtten, Hirai, or Tabushi). Depending on the CD molecule used, the substrate to be catalyzed, and the reaction intended, the recognition site and catalytic groups can be provided through one or several derivatives, as needed. The recognition site generally involves the hydrophobic cavity of the CD molecule, and provides a means for specifically binding and/or orienting the substrate of interest with the CD catalytic agent.

The catalytic groups are generally organic and/or inorganic chemical residues, functional groups and ionic species that provide a suitable chemical environment for promoting the catalytic reaction. The catalytic groups can be any known chemical residue or species that provides the desired catalytic reaction, including carboxylates, imidazoles, histamines, hydroxyls, amines, amides, aldehydes, ketones, phosphates, sulfhydryls, halogens, amino acids, nucleic acids, chelators, and metals. Additional examples of suitable catalytic groups useful in the instant invention can be found in the art of derivatizing CD's and derivatizing or "genetic engineering" of antibodies for use as enzymes. Other suitable references are; M. L. Bender, I. Tabushi, E. Baldwin, P. G. Schultz (below).

In addition, an improved CD catalyst agent can be synthesized wherein the recognition site and/or catalytic groups is provided or augmented through the use of one or more suitable captured guests, described herein, that interact (e.g. binding, alignment and/or excimer formation), with the substrate being catalyzed. In this case, the captured guest is preferably coupled to the CD molecule by a suitable spacer group to allow interaction with the substrate, and can be any suitable aliphatic, aromatic, or heterocyclic compound, including any suitable inclusion compounds described herein.

Suitable CD catalyst agent reactions include hydrolysis (e.g. of any suitable ester or amide containing substrates), oxidation, dephosphorylation, acid-base catalysis, formylation, dichloromethylation, carboxylation, rearrangement, substitution, allylation, and halogenation, among others. In any case, the catalyst CD agents can be prepared so that the catalyst CD product is inhibitory or toxic to certain cells, microbes or parasites. The cyclodextrin catalyst agents can also be coupled to a variety of substances, such as biorecognition molecules, ligands, antigens, antibodies, nucleotides, nucleic acids, and liposomes, as well as to a variety of support materials including magnetic particles for use in assays and chemical processes.

An improved CD catalyst agent comprises the direct or indirect coupling of any suitable antenna substance described herein, to the CD molecule, for collection of light energy that is transferred to the CD catalyst and thereby accelerates the desired reaction such as in photodynamic therapy.

PREPARATION XIII

Amylose Polymer Carriers

Also, the helical segments of amyloses, can be suitably polymerized, derivatized and/or capped to include captured guests, and antenna substances as needed, to modulate wavelength response and/or emission. Also, they can be in the form of a drug carrier wherein suitable functional and/or coupling groups are included. Yet another composition includes the use of "self assembly" substances coupled to the amylose.

Suitably, these amylose polymers have the necessary properties to form an inclusion complex with the a drug or other active agent and can be used to produce new and useful compositions. Preferred substances are soluble or colloidal polymers of helical segments of amyloses. Especially useful are helical amylose molecules of more than 5 and less than 120 glucose units, that favor formation of rigid linear helixes.

In one preferred embodiment, a suitable amylose polymer is formed from segments that have included a drug. Then the amylose is suitably cross-linked using various bifunctional cross-linking agents so that the amylose polymer cannot release the entrapped drug. Another preferred embodiment has incorporated cross-links that contain biocleavable linkages as described previously.

Helical amylose polymers can be targeted by coupling them to biorecognition molecules such as proteins, lipids, lipoproteins, nucleic acids, surfactants, virus coat proteins, and organic molecules. They can include intermediate substances of acrylamides (HPMA), nylons, polystyrenes, resins, metals and celluloses, and combinations of these.

PREPARATION XIV

Micelle Polymer Carriers with Controlled Release

A micelle polymer carrier is a new invention defined herein as a water soluble (or colloidal) micelle that has been suitably polymerized so that it completely entraps a drug or other active agent within. The formation of micelles for carrying drugs is well known. However, micelle carriers of the prior art suffer from uncontrolled loss of the drug due to diffusion. This invention solves that problem through cross-linking the micelle components to completely entrap the drug until it is delivered to the site of action.

For this invention, any suitable technology now used to for preparing drug-carrying micelles is applicable to the synthesis of this invention including disclosures of reagents for preparing liposomes and those of Alkan-Onyuksel, H., Pharmaceutical Res. 11, 206–212 (1994). A distinguishing property of this invention is that the micelle-forming components must have suitable functional groups available on their hydrophilic "heads" to permit cross-linking after the micelle has been formed with a drug inside.

In one preferred embodiment, suitable micelles are formed that contain a drug. Then the head groups in the hydrophilic surface are suitably cross-linked using various bifunctional cross-linking agents so that the micelle cannot release the entrapped drug. Another preferred embodiment has incorporated cross-links that contain biocleavable linkages as described previously. Also, this carrier can be suitably targeted by coupling suitable biorecognition molecules to the surface.

While the invention has been described with reference to certain specific embodiments, it is understood that changes may be made by one skilled in the art and it would not thereby depart from the spirit and scope of the invention which is limited only by the claims appended hereto.

What is claimed is:

1. A method for producing a controlled release pharmaceutical composition comprising;

a) combining cyclodextrin molecules selected from the group consisting of cyclodextrin derivatives, cyclodextrin dimers, cyclodextrin trimers, and cyclodextrin polymers with an active agent selected from the group consisting of anticancer drugs, antineoplastic drugs, antifungal drugs, antibacterial drugs, antiviral drugs, cardiac drugs, neurological drugs, alkaloids, antibiotics, bioactive peptides, steroids, steroid hormones, polypeptide hormones, interferons, interleukins, narcotics, prostaglandins, purines, pyrimidines, anti-protozoan drugs and anti-parasitic drugs to form an inclusion complex between the cyclodextrin molecules and the active agent, and b) covalently cross-linking the cyclodextrin molecules through a biocleavable linkage selected from the group consisting of a disulfide linkage, a protected disulfide linkage, an ester linkage and a hydrazone linkage, to form a polymer that has completely entrapped the active agent and wherein the cross-linking provides the function of controlled release.

2. The method of claim 1 further comprising the step of coupling a biorecognition molecule to the pharmaceutical.

3. The method of claim 1 wherein the active agent is selected from the group consisting of ganciclovir, furosemide, indomethacin, chlorpromazine, methotrexate, penicillin derivatives, anthracyclines, teramycins, tetracyclines, chlorotetracyclines, clomocyclines, butoconazole, ellipticines, guamecyclines, macrolides, filipins, fungichromins, nystatins, 5'-fluorouracil, 5'-fluoro-2'-deoxyuridine, allopurinol and paclitaxel.

4. A method for producing a controlled release pharmaceutical composition comprising;

a) combining cyclodextrin molecules selected from the group consisting of cyclodextrin derivatives, cyclodextrin dimers, cyclodextrin trimers, and cyclodextrin polymers with an active agent consisting of a nucleic acid, to form an inclusion complex between the cyclodextrin molecules and the active agent, and b) covalently cross-linking the cyclodextrin molecules through a biocleavable linkage selected from the group consisting of a disulfide linkage, a protected disulfide linkage, an ester linkage and a hydrazone linkage, to form a polymer that has completely entrapped the active agent and wherein the cross-linking provides the function of controlled release.

5. The method of claim 4 further comprising the step of coupling a biorecognition molecule to the pharmaceutical.

6. The method of claim 4 wherein the nucleic acid is selected from the group consisting of DNA, RNA, antisense oligonucleotides, phosphorthioate oligonucleotides, synthetic nucleic acid polymers and peptide nucleic acids.

7. A method for producing a controlled release pharmaceutical composition comprising;

a) combining cyclodextrin molecules selected from the group consisting of cyclodextrin derivatives, cyclodextrin dimers, cyclodextrin trimers, and cyclodextrin polymers with an active agent consisting of a toxin, to form an inclusion complex between the cyclodextrin molecules and the active agent, and b) covalently cross-linking the cyclodextrin molecules through a biocleavable linkage selected from the group consisting of a disulfide linkage, a protected disulfide linkage, an ester linkage and a hydrazone linkage, to form a polymer that has completely entrapped the active agent and wherein the cross-linking provides the function of controlled release.

8. The method of claim 7 further comprising the step of coupling a biorecognition molecule to the pharmaceutical.

9. The method of claim 7 wherein the toxin is selected from the group consisting of aflatoxins, ricins, bungarotoxins, irinotecan, pesticides, cevadines, desatrines, veratridine and cevine derivatives.

* * * * *